(12) United States Patent
Chaput et al.

(10) Patent No.: US 9,358,121 B2
(45) Date of Patent: Jun. 7, 2016

(54) ARTIFICIAL DISC WITH UNIQUE ARTICULATING GEOMETRY AND ASSOCIATED METHODS

(75) Inventors: Christopher Chaput, Belton, TX (US); Robert J. Jones, Austin, TX (US)

(73) Assignee: SpineSmith Partners, L.P., Austin, TX (US)

( * ) Notice: Subject to any disclaimer, the term of this patent is extended or adjusted under 35 U.S.C. 154(b) by 959 days.

(21) Appl. No.: 11/684,608

(22) Filed: Mar. 10, 2007

(65) Prior Publication Data
US 2008/0221689 A1    Sep. 11, 2008

(51) Int. Cl.
*A61F 2/44*    (2006.01)
*A61F 2/30*    (2006.01)

(52) U.S. Cl.
CPC ......... *A61F 2/4425* (2013.01); *A61F 2002/305* (2013.01); *A61F 2002/3092* (2013.01); *A61F 2002/30224* (2013.01); *A61F 2002/30331* (2013.01); *A61F 2002/30365* (2013.01); *A61F 2002/30369* (2013.01); *A61F 2002/30484* (2013.01); *A61F 2002/30507* (2013.01); *A61F 2002/30578* (2013.01); *A61F 2002/30607* (2013.01); *A61F 2002/30616* (2013.01); *A61F 2002/30662* (2013.01); *A61F 2002/30841* (2013.01); *A61F 2002/30878* (2013.01); *A61F 2002/30894* (2013.01); *A61F 2002/443* (2013.01); *A61F 2220/0025* (2013.01); *A61F 2220/0033* (2013.01); *A61F 2230/0069* (2013.01); *A61F 2250/0062* (2013.01); *A61F 2310/00011* (2013.01)

(58) Field of Classification Search
USPC .......................................... 623/17.11–17.16
See application file for complete search history.

(56) References Cited

U.S. PATENT DOCUMENTS

| | | | |
|---|---|---|---|
| 5,314,477 A | 5/1994 | Marnay | ........................... 623/17 |
| 5,401,269 A | 3/1995 | Buttner-Janz et al. | .......... 623/17 |
| 5,556,431 A | 9/1996 | Buttner-Janz | ................... 623/17 |
| 5,931,674 A * | 8/1999 | Hanosh | ............... A61C 8/0033 433/173 |
| 6,039,763 A | 3/2000 | Shelokov | ........................ 623/17 |
| 6,117,173 A * | 9/2000 | Taddia et al. | .............. 623/16.11 |

(Continued)

FOREIGN PATENT DOCUMENTS

| | | | | |
|---|---|---|---|---|
| EP | 0560141 | 9/1993 | ............... | A61F 2/44 |
| EP | 1712207 | 10/2006 | ............... | A61F 2/44 |

(Continued)

OTHER PUBLICATIONS

Charite Artificial Disc—Technical Monograph, DePuySpine, copyright 2004.

(Continued)

*Primary Examiner* — Matthew Lawson
(74) *Attorney, Agent, or Firm* — Winstead PC

(57) ABSTRACT

An apparatus and method is provided relating to artificial discs. An artificial disc is provided that facilitates simultaneous and independent articulation of flexion/extension, lateral bending, anterior/posterior translation, and axial rotation. The artificial disc provides these four simultaneous and independent articulations by independently addressing each type of articulation in the design of the artificial disc. In one example, an artificial disc is comprised of a bearing disposed between first and second end plates. The bearing is movable relative to each end plate, independent of the other end plate. The end plates are affixed to adjacent vertebrae.

33 Claims, 15 Drawing Sheets

(56) References Cited

U.S. PATENT DOCUMENTS

| | | | |
|---|---|---|---|
| 6,368,350 B1 | 4/2002 | Erickson et al. | 623/17.14 |
| 6,375,683 B1 | 4/2002 | Crozet et al. | 623/17.15 |
| 6,517,580 B1 | 2/2003 | Ramadan et al. | 623/17.15 |
| 6,579,320 B1 | 6/2003 | Gauchet et al. | 623/17.15 |
| 6,723,097 B2 | 4/2004 | Fraser et al. | 606/61 |
| 6,726,720 B2 | 4/2004 | Ross et al. | 623/17.15 |
| 6,733,532 B1 | 5/2004 | Gauchet et al. | 623/17.12 |
| 6,740,118 B2 | 5/2004 | Eisermann et al. | 623/17.14 |
| 6,896,676 B2 | 5/2005 | Zubok et al. | 606/61 |
| 6,966,929 B2* | 11/2005 | Mitchell | A61F 2/4425 623/17.11 |
| 6,994,727 B2 | 2/2006 | Khandkar et al. | 623/17.15 |
| 7,001,432 B2 | 2/2006 | Keller et al. | 623/17.14 |
| 7,048,764 B2 | 5/2006 | Ferree | 623/17.15 |
| 7,060,097 B2 | 6/2006 | Fraser et al. | 623/17.11 |
| 7,083,649 B2 | 8/2006 | Zucherman et al. | 623/17.11 |
| 2002/0128715 A1 | 9/2002 | Bryan et al. | 623/17.15 |
| 2002/0143399 A1 | 10/2002 | Sutcliffe | 623/17.11 |
| 2003/0199983 A1 | 10/2003 | Michelson | 623/17.16 |
| 2003/0208273 A1 | 11/2003 | Eisermann et al. | 623/17.14 |
| 2004/0102846 A1 | 5/2004 | Keller et al. | 623/17.11 |
| 2004/0143332 A1 | 7/2004 | Krueger et al. | 623/17.14 |
| 2004/0243240 A1 | 12/2004 | Beaurain et al. | 623/17.14 |
| 2004/0243241 A1 | 12/2004 | Istephanous et al. | 623/17.14 |
| 2005/0113926 A1 | 5/2005 | Zucherman et al. | 623/17.14 |
| 2005/0159818 A1* | 7/2005 | Blain | 623/17.15 |
| 2005/0197706 A1 | 9/2005 | Hovorka et al. | 623/17.15 |
| 2005/0216081 A1* | 9/2005 | Taylor | 623/17.11 |
| 2005/0216086 A1* | 9/2005 | Marik et al. | 623/17.15 |
| 2005/0240272 A1* | 10/2005 | Zubok et al. | 623/17.15 |
| 2005/0240273 A1* | 10/2005 | Khandkar et al. | 623/17.15 |
| 2005/0246024 A1 | 11/2005 | Zeegers | 623/17.15 |
| 2005/0256578 A1* | 11/2005 | Blatt et al. | 623/17.15 |
| 2005/0261772 A1* | 11/2005 | Filippi et al. | 623/17.13 |
| 2005/0283242 A1* | 12/2005 | Zucherman | A61F 2/4425 623/17.15 |
| 2006/0004453 A1 | 1/2006 | Bartish, Jr. et al. | 623/17.15 |
| 2006/0041313 A1* | 2/2006 | Allard et al. | 623/17.15 |
| 2006/0041314 A1* | 2/2006 | Millard | 623/17.16 |
| 2006/0116768 A1 | 6/2006 | Krueger et al. | 623/17.14 |
| 2006/0122703 A1* | 6/2006 | Aebi et al. | 623/17.15 |
| 2006/0136063 A1 | 6/2006 | Zeegers | 623/17.14 |
| 2006/0149258 A1* | 7/2006 | Sousa | A61F 2/0811 623/13.12 |
| 2006/0149372 A1* | 7/2006 | Paxson et al. | 623/17.11 |
| 2006/0178745 A1 | 8/2006 | Bartish, Jr. et al. | 623/17.13 |
| 2006/0178746 A1 | 8/2006 | Bartish, Jr. et al. | 623/17.13 |
| 2006/0212123 A1* | 9/2006 | Lechmann et al. | 623/17.15 |
| 2006/0235526 A1* | 10/2006 | Lemaire | 623/17.14 |
| 2007/0038219 A1 | 2/2007 | Matthis et al. | 606/72 |
| 2007/0162137 A1* | 7/2007 | Kloss et al. | 623/17.15 |
| 2007/0179613 A1* | 8/2007 | Heinz | 623/17.12 |
| 2007/0225813 A1 | 9/2007 | Haines | 623/17.16 |
| 2007/0276495 A1* | 11/2007 | Aaron | 623/17.12 |
| 2008/0058940 A1* | 3/2008 | Wu | A61F 2/4425 623/17.15 |
| 2008/0221690 A1 | 9/2008 | Chaput et al. | 623/17.16 |
| 2008/0221691 A1 | 9/2008 | Chaput et al. | 623/17.16 |
| 2009/0076616 A1* | 3/2009 | Duggal et al. | 623/17.16 |

FOREIGN PATENT DOCUMENTS

| | | | |
|---|---|---|---|
| WO | WO 2004/002291 | 1/2004 | |
| WO | WO 2004/039240 | 5/2004 | |
| WO | WO 2004/039241 | 5/2004 | |
| WO | WO 03/005939 | 1/2009 | A61F 2/44 |

OTHER PUBLICATIONS

Mobi-C Brochure, LDR Holding Corporation, Publication date unknown, 2008 Copyright notice.

Prodisc-C Total Disc Replacement Product Information, Synthes Spine, Publication date unknown 2008 Copyright notice.

\* cited by examiner

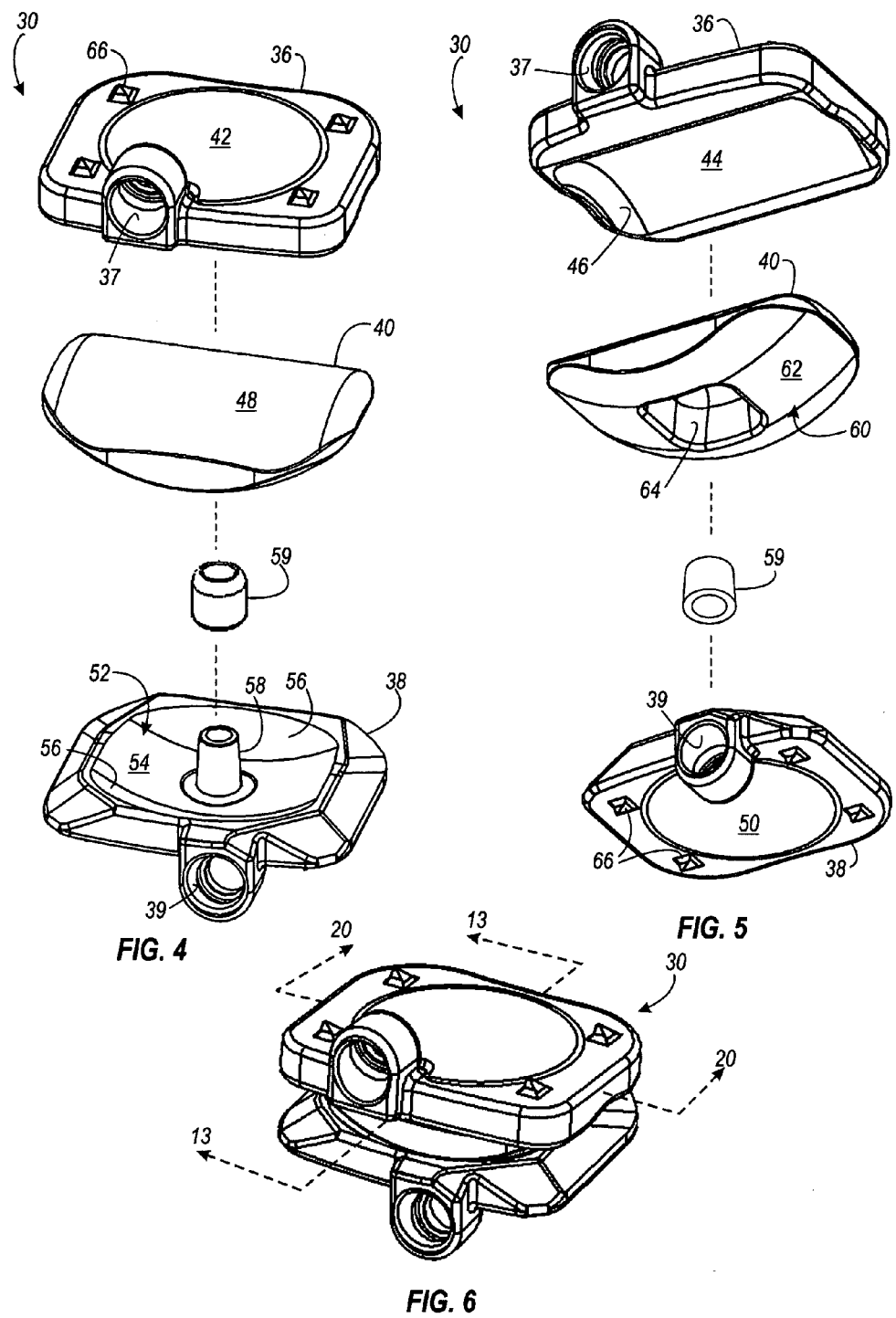

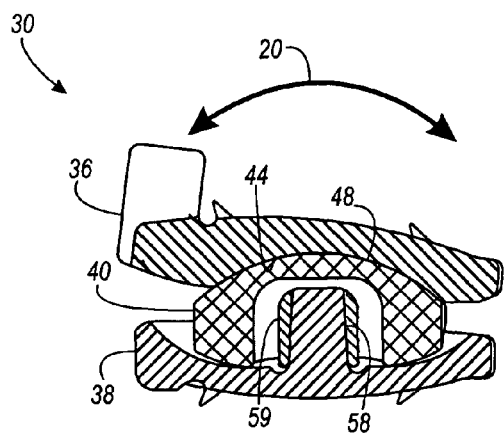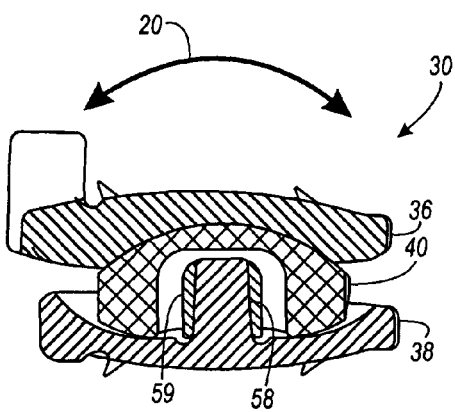
FIG. 13    FIG. 14
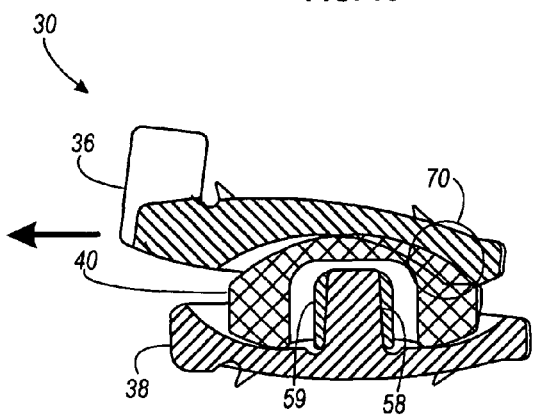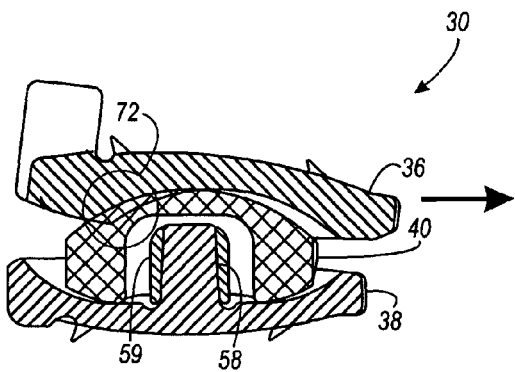
FIG. 15    FIG. 16

ARTIFICIAL DISC WITH UNIQUE ARTICULATING GEOMETRY AND ASSOCIATED METHODS

FIELD OF THE INVENTION

This invention relates to the field of surgical implants. In particular, this invention is drawn to artificial discs, artificial disc replacements, and associated methods.

BACKGROUND OF THE INVENTION

The spine can be considered to be a series of joints made up of vertebrae and discs. Due to trauma, disease, and/or aging, the spine may be subject to degeneration. This degeneration may destabilize the spine and cause pain and/or nerve damage. Medical procedures are often required to either ease back pain, repair damage, or to prevent future damage.

One procedure that is often used to treat back pain or spinal damage is spinal fusion. Spinal fusion is a surgical technique used to combine two or more adjacent vertebrae. Supplemental bone tissue is used in conjunction with the patient's natural osteoblastic processes in a spinal fusion procedure. Spinal fusion is used primarily to eliminate back pain caused by the motion of the damaged vertebrae by immobilizing adjacent vertebrae. Conditions for which spinal fusion might be done include degenerative disc disease, treatment of a spinal tumor, a vertebral fracture, scoliosis, degeneration of the disc, spondylolisthesis, or any other condition that causes instability of the spine. One problem with a spinal fusion procedure is that, while the two fused vertebrae rarely detach from each other, the fusion procedure causes additional risk of damage to the adjacent vertebrae. Also, since the fused vertebrae can no longer move relative to one another, the spine can no longer provide the motion afforded by a healthy spine.

One alternative to spinal fusion is artificial disc replacement. Artificial disc replacement is a medical procedure in which degenerated or damaged discs in the spine are replaced with artificial ones. Like with a spinal fusion, an artificial disc replacement procedure is primarily used to treat back or neck pain, pain radiating into the extremities, and/or treat a spine damaged from degenerative disc disease. One goal of an artificial disc replacement is to eliminate back pain, while allowing normal spinal motion. One advantage over spinal fusion is that an artificial disc may prevent premature breakdown of adjacent vertebrae resulting from a spinal fusion procedure. One problem with artificial disc replacement procedures is that the artificial disc does not provide the same type of motion that a healthy disc does. Ideally, an artificial disc should allow the vertebral bodies to move relative to one another in a manner that provides an equivalent motion afforded by a healthy intervertebral disc, in such a way that the movement of the spine approximates the natural movement of a healthy spine. However, typical artificial discs allow some motion, but do not adequately approximate the natural movement of a healthy spine.

There is therefore a need for an artificial disc and related replacement procedure that adequately treats degenerative disc disease and other spinal conditions, while also enabling natural spinal articulations.

SUMMARY OF THE INVENTION

A surgical implant configured to be inserted between two vertebrae includes a first member configured to be attachable to a first vertebrae, a second member configured to be attachable to a second vertebrae, and a third member disposed between the first and second members to form an articulating artificial disc, wherein the first, second, and third members are configured to allow the artificial disc simultaneous and independent articulation of flexion/extension, lateral bending, anterior/posterior translation, and axial rotation.

One embodiment includes a first member configured to be attachable to a first vertebrae, the first member having a first concave surface, a second member configured to be attachable to a second vertebrae, the second member having a second concave surface, a third member disposed between the first and second members, the third member having first and second convex surfaces configured to engage the first and second concave surfaces, respectively. The first convex surface of the third member and the first concave surface of the first member are configured to facilitate flexion/extension of the surgical implant, wherein the second convex surface of the third member and the second concave surface of the second member are configured to facilitate lateral bending, translation, and rotation of the artificial disc.

Another embodiment of the invention provides a method for providing an artificial disc to treat a damaged disc in a spine including providing a first member configured to be attachable to a first vertebrae, providing a second member configured to be attachable to a second vertebrae, forming a third member between the first and second members, and configuring the first and second members and the third member to allow the artificial disc simultaneous and independent articulation of flexion/extension, lateral bending, anterior/posterior translation, and axial rotation.

Another embodiment of the invention provides a surgical implant configured to be inserted between two vertebrae including a first member configured to be attachable to a first vertebrae, a second member configured to be attachable to a second vertebrae, a third member disposed between the first and second members, wherein the third member has a first surface configured to engage the first member to facilitate movement of the surgical implant about a first axis, wherein the third member has a second surface configured to engage the second member to facilitate movement about a second axis, wherein the first and second axes are substantially perpendicular to one another, and wherein the first and second members are movable relative to one another to facilitate anterior/posterior translation, and axial rotation.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which:

FIGS. 4 and 5 are exploded isometric views of an artificial disc of the present invention.

FIG. 6 is an assembled view of the artificial disc shown in FIGS. 4 and 5.

FIGS. 13-16 are sectional diagrams taken along line 13-13 of FIG. 6, with one end plate shown in different positions.

DETAILED DESCRIPTION

Figure 1:
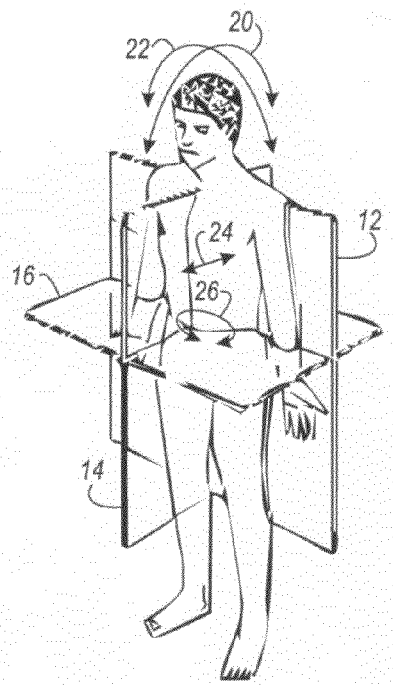
FIG. 1 is a diagram illustrating the anatomical planes of the body and various articulations.

The present invention relates to artificial disc replacement and related replacement procedures. The invention introduces the concept of variable constraint disc replacement, of which there are two components. The first component is immediate fixation (the resistance to displacement of the prosthetic endplates in relation to the vertebrae at the time of insertion). In one example, this is exemplified in the fixation to the endplates using either barbed teeth alone or with optional peg fixation. While barbed teeth will provide fixation for the majority of motion segments, use of the peg fixation provides more initial constraint to motion at the prosthesis-bone interface and thus enhances immediate fixation in the setting where the surgeon is concerned that micromotion may limit growth of bone in and around the bone-implant interface (osseointegration) and negatively impact long term implant stability (the absence of change of position of the implant on radiographs over time). Good initial stability at the bone-implant interface has been recognized as desirable for the long term success of hip and knee replacements, and the same concerns exist with any motion preservation device. This is particularly true in the spine where neurologic, vascular, and gastrointestinal function can be compromised by migration of an implant. The ability of a surgeon to compensate for problems encountered in locally variable anatomy, surgical technique, and preoperative motion are currently very limited. The design features of the present invention address the range of pathology seen in clinical practice and avoid catastrophic failure or migration of a particular implant.

The second component of variable constraint applies to the motion of the prosthesis obtained after implantation at a particular motion segment (segmental motion or articulation). Motion at a particular segment (articulation) varies between levels and varies at the same level between genders, races, age groups, and extent of degeneration (arthritis). Current implants typically take a one motion fits all approach, which does not reflect the variables mentioned above. In order to re-create physiologic motion that varies between the particular spinal level and the particular pathology seen at that level, the surgeon must have options to add or take away constraints to motion intraoperatively. There is a clear precedent in knee arthroplasty where the amount of resection of the normal structures in combination with the pre-operative deformity is the major determinant in selecting the amount of constraint required in a prosthetic joint for a particular patient. This concept in joint replacement is sometimes referred to "balance" and reflects a surgeon's attempt to recreate normal range of motion intraoperatively by altering implant components or releasing soft tissue restraints to motion.

For example, the lumbar segment (articulation) comprised of the disc, ligaments and joints between the fourth and fifth lumbar and also the fourth and fifth cervical vertebrae have been documented to have an increased propensity for anterior translation with increasing degeneration. Placement of a disc at these levels that is designed to allow for normal anterior translation that is an average of that seen at multiple segments may lead, in the long term, to catastrophic failure of the implant since the segment tends to have increased motion with age and degenerative change.

There are reports of this type of failure in some lumbar disc replacements, and an increase in motion above that seen in the normal spine can lead to pain, numbness, and even paralysis. This issue may be magnified, because in order to insert any prosthetic disc, some of the normal constraints to motion (the annulus, disc material, posterior longitudinal ligament, and uncovertebral ligaments) need to be resected during implantation.

Thus, surgeons need to have the ability to tailor constraint to the accepted definition of normal motion for a particular spinal motion segment, the amount of normal tissue sacrificed at the time of neural decompression or implant insertion, and the pathology visible on pre-operative imaging of the motion segment. The present invention allows a surgeon to place the implant, take the spine through a normal range of motion and assess the motion at implant site. Since the invention is modular, both the height of the inner core and the size and shape of the collar could be changed to decrease or increase motion through the replaced disc. Increasing disc height would lead to additional tension on the soft tissue restraints and limit motion, and a larger collar would restrict translation of the upper prosthetic endplate in relation to the lower one. In this manner, a spinal surgeon is enabled to utilize the concept of balanced motion already well established in other joint replacement surgery.

In one example, the invention applies to artificial disc replacement performed through an anterior approach. Generally, the present invention provides an artificial disc configured to attach between two adjacent vertebrae. In one example, the artificial disc is comprised of a first member attached is a first vertebrae, a second member attached is a second adjacent vertebrae, and a third member disposed between the first and second members (described in detail below). The artificial disc of the present invention facilitates simultaneous and independent articulation of flexion/extension, lateral bending, anterior/posterior translation, and axial rotation. An artificial disc of the present invention provides these four simultaneous and independent articulations by independently addressing each type of articulation in the design of the artificial disc. In addition, various articulations are constrained to approximate the natural movement of the spine. Various articulations are also restricted to prevent damage to the spine, arteries, and nerves when excessive stress is applied to the artificial disc.

In order to fully appreciate the following description, it is useful to understand various articulations of spinal joints. The articulations will be described with reference to the anatomical planes of the body. FIG. 1 is a diagram illustrating the three anatomical planes of the body. The coronal plane 12 (frontal plane) is a vertical plane running from side to side that divides the body, or any of its parts, into anterior and posterior portions. The sagittal plane 14 (lateral plain) is a vertical plane running from front to back that divides the body, or any of its parts, into right and left sides. When the sagittal plane 14 crosses through the midline of the body (as shown in FIG. 1), it divides the body or any of its parts into right or left halves, and is known as a median plane. The axial plane 16 (transverse plane) is a horizontal plane that divides the body, or any of its parts, into upper and lower parts.

FIG. 1 also includes indications various articulations. A first type of articulation that is referenced below is flexion-extension. Flexion-extension is a movement from front to back along the sagittal plane 14, such as the movement of nodding your head. Flexion-extension is illustrated in FIG. 1 by line 20. A second type of articulation that is referenced below is lateral bending. Lateral bending is a movement from side to side (perpendicular to flexion) along the coronal plane 12. Lateral bending is illustrated in FIG. 1 by line 22. A third type of articulation that is referenced below is translation. Translation is a sliding motion from front to back along the sagittal plane 14 or the transverse plane 16. This articulation may also be referred to as either anterior translation (translation toward the anterior of the body) or posterior translation (translation toward the posterior of the body). Translation is illustrated in FIG. 1 by line 24. A fourth type of articulation that is referenced below is axial rotation. Axial rotation is a rotating motion about an axis that is perpendicular to the transverse plane 16. Axial rotation is illustrated in FIG. 1 by line 26.

Figure 2:
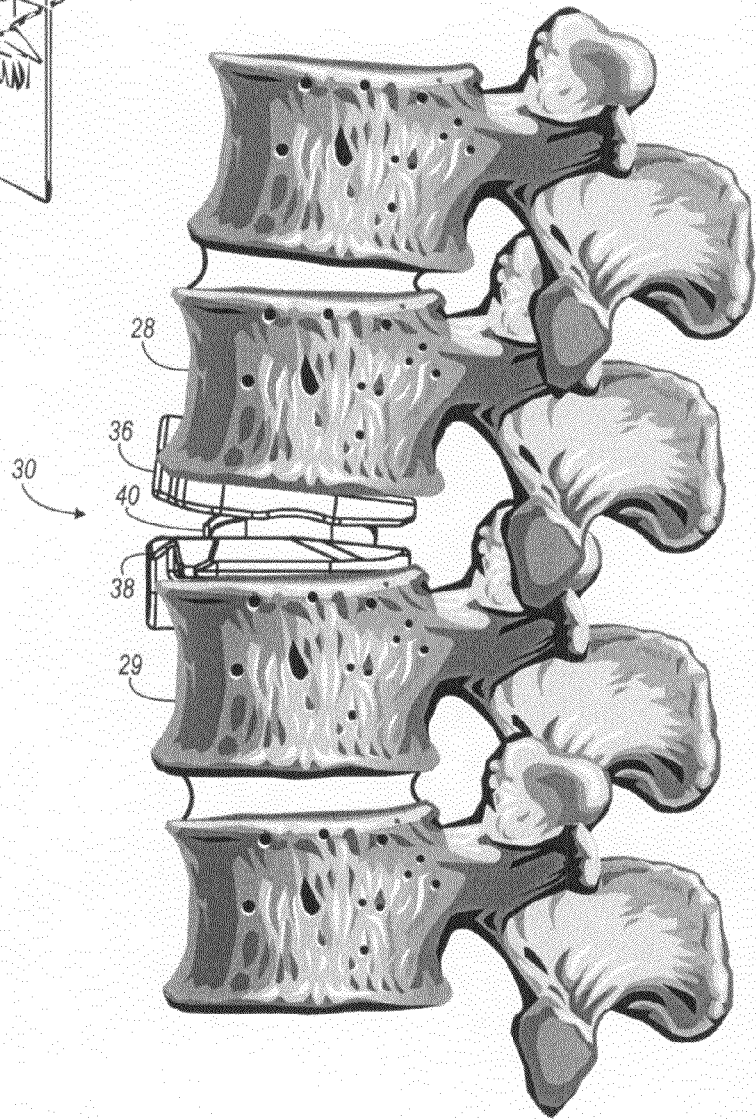
FIG. 2 is a side view showing a portion of a spine with an artificial disc of the present invention installed between two vertebrae.

FIG. 2 is a side view showing a portion of a spine with an artificial disc of the present invention installed between two adjacent vertebrae. As shown, an artificial disc 30 is inserted in between a first vertebrae 28 and a second vertebrae 29. The artificial disc 30 is comprised of first and second end plates 36 and 38 and a bearing 40. The first end plate 36 is affixed to the first vertebrae 28. The second end plate 38 is affixed to the second vertebrae 29. The end plates 36 and 38 may be attached to the vertebrae in any suitable manner, examples of which are given below. The bearing 40 is positioned between the first and second end plates 36 and 38, and engages each. The bearing 40 is movable in various ways, relative to the first and second end plates 36 and 38 (described in detail below). In addition, the bearing 40 is movable relative to each end plate, independent of the other end plate. In other words, movement of the bearing 40 relative to the first end plate 36 is independent of movement of the bearing 40 relative to the second end plate 38. These relative and independent movements between the end plates 36 and 38 and the bearing 40 are what allow the artificial disc 40 simultaneous and independent articulations of flexion/extension, lateral bending, anterior/posterior translation, and axial rotation.

Figure 3:
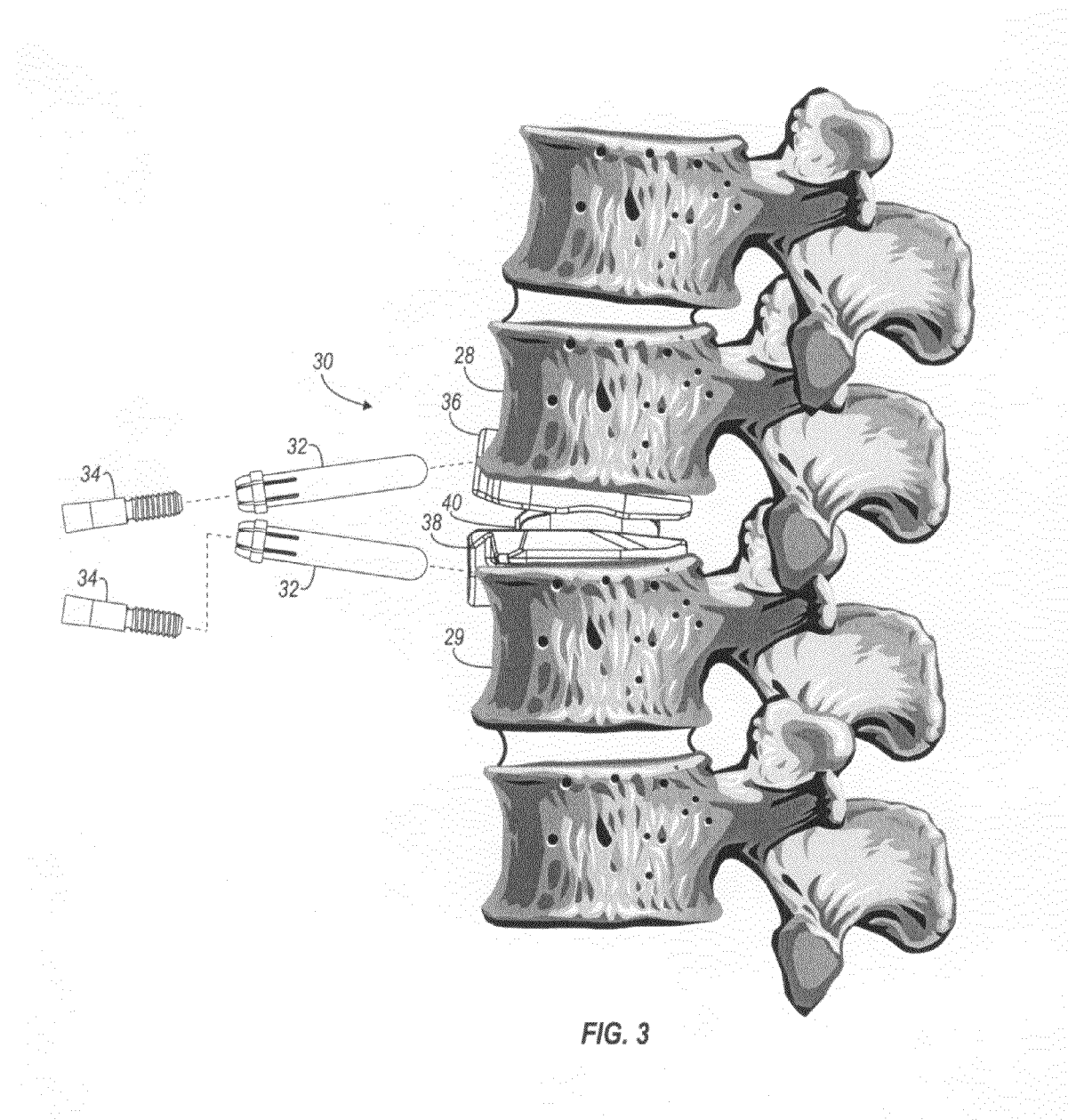
FIG. 3 is a side view of the artificial disc of FIG. 2 shown with fasteners in an exploded view.

FIG. 3 is an exploded side view of the spine and artificial disc of FIG. 2. In this example, the artificial disc 30 is affixed to the vertebrae 28 and 29 using pegs 32 and locking screws 34. The fixation to the bone using the pegs 32 and locking screws 34 is described in detail below. Generally, after the artificial disc 30 is inserted as shown in FIGS. 2 and 3, the surgeon will drill holes through openings formed in the artificial disc 30 and into the vertebrae. Next, the pegs 32 are inserted into the holes. Finally, the locking screws 34 are screwed into the pegs 32 to lock the pegs 32 in place. Advantages of the pegs over other types of bone fixation include less assembly migration of the implant, and that the peg is mechanically stronger than a screw of a similar diameter.

The artificial disc 30 may be made from any suitable material. In one example, the first and second end plates are made of a metal such as a CoCr alloy, stainless steel, titanium, etc., or any of these materials coated with wear resistant material or material treatment, etc. In one example, the bearing 40 is made of ultra high molecular weight polyethylene (UHMWPE), or any other suitable material.

While an artificial disc of the present invention can be configured and implemented in numerous ways, following are some general guidelines which are provided as an example only. For example, the ranges given below are merely examples, as any desired ranges can be implemented.

The bearing of the artificial disc has radii of curvature in both the sagittal and coronal planes. The two curved surfaces, on opposite sides of the bearing, allow the artificial disc independent and simultaneous flexion/extension and lateral bending. This is described in detail below. The curved surfaces, and the inner surfaces of the end plates maintain a controlled and desired position while allowing motion that constrains the device from subluxation.

In this example, flexion/extension articulation in the sagittal plane is unrestricted. At the same time, curved surfaces constrain and prevent anterior and posterior subluxation. The configuration of the artificial disc also allows anterior/posterior translation articulation to be unrestricted over a certain range, and constrained over another range. In one example, anterior/posterior translation is unrestricted within approximately +/−0.5 mm and constrained out to approximately +/−1.0 mm. Also in this example, the artificial disc has a nominal 7° anatomic posterior slope with a range of motion of approximately +/−5°.

In this example, lateral bending articulation in the coronal plane is unrestricted. At the same time, curved surfaces constrain and prevent medial lateral subluxation/translation. In one example, the artificial disc has a lateral bending range of motion of approximately +/−5°.

In this example, axial rotation articulation in the coronal or transverse planes is restricted and constrained. In one example, the artificial disc has an axial rotation range of motion of approximately +/−5°.

With respect to safety, these exemplary guidelines include considerations relating to sizing, bone fixation, etc. . . . Ideally, the bearing of the artificial disc should be contained safely within the end plates with consideration to failure modes of the device. With respect to size and shape of the artificial disc, in one example, the end plates are domed to match anatomic end plate concavity. This convex shape on the end plates will help with the fixation to the vertebrae. Also, the transverse plane footprint of the artificial disc, relative to the sagittal plane, should be lordosed in the cervical and lumbar spinal regions and kyphosed in the thoracic spinal region to match pure anatomic positioning.

With respect to bone fixation, the first and second end plates may include teeth which are used to resist anterior extrusion. Also, the end plate outer surfaces may include a porous ingrowth interface to help new bone fixation. In one example, peg or screw fixation may be used to resist anterior/posterior or medial/lateral extrusion.

Note that, throughout this description, when terms such as "upper" or "lower" are used, they are relative terms merely used to describe the figures as oriented in the drawings. For example, if a component is referred to as an "upper" component, the scope of the invention is not restricted to that component being used in a literally "upper" position. Likewise, in some potential applications (e.g., a disc replacement procedure for an animal) where the spine is normally oriented horizontally, the terms "upper" and "lower" are also relative and do not limit the scope of the invention.

FIGS. 4 and 5 are exploded isometric views of an artificial disc of the present invention. FIG. 4 shows an artificial disc 30, including a first end plate 36, a second end plate 38, a bearing 40, and a collar 59. FIG. 5 shows is the same artificial disc 30, but from another angle, to see the opposite sides of the end plates 36 and 38 and bearing 40.

The first end plate 36 has a hole 37 formed to facilitate bone fixation using pegs or screws (described below). The first end plate 36 has a convex outer surface 42 which, as mentioned above, is configured to match the surface of the adjacent vertebrae. The first end plate 36 has a concave inner surface 44, which, in this example, has a cylindrically curved shape with closed ends 46. The bearing 40 has a convex upper surface 48, which has a cylindrically shaped curve. The upper surface 48 of the bearing 40 is configured to closely match the inner surface 44 of the end plate 36. As is described in detail below, the configuration of the interface between the upper surface 48 of the bearing 40 and of the inner surface 44 of the end plate 36 enables the artificial disc 30 to have flexion/extension articulation.

The second end plate 38 has a hole 39 formed to facilitate bone fixation using pegs or screws. The second end plate of 38 has a convex outer surface 50 which, like the outer surface 42 of the end plate 36, is configured to match the surface of the adjacent vertebrae. The second end plate 38 also has a concave inner surface 52. However, the concave inner surface 52 is more complex than the concave inner surface 44 of the end plate 36. The inner surface 52 has a middle portion 54 that has a cylindrically shaped curve, and opposite outer portions 56, which are bowl shaped. Within the inner surface 52, a protrusion or post 58 extends upward.

The bearing 40 has a convex lower surface 60. The lower surface 60 of the bearing 40 includes a middle portion 62 that has a cylindrically shaped surface. The middle portion 62 is configured to closely match the middle portion 54 of the inner surface 52 of the end plate 38 to enable unconstrained lateral bending articulation. However, to facilitate anterior/posterior translation (described in detail below), the width of the middle portion 54 of the end plate 38 is greater than the width of the middle portion 62 of the bearing 40. This enables unconstrained translation articulation over a range that is approximately equal to the difference between the width of the middle portions 62 and 52.

A collar 59 is shown between the second end plate 38 and the bearing 40. The collar 59 is configured to fit over the post 58. As described below, different sized and shaped collars may be used to control various degrees of change in articulation. Alternately, the post 58 can be sized as desired, and used without a collar.

The bearing 40 includes a recess 64 formed in the lower surface 60. The recess 64 is adapted to receive the post 58 and collar 59 when the artificial disc 30 is assembled. In the examples shown in the drawings, the recess 64 does not extend all the way through the bearing 40. However, in other examples, the recess 64 could extend all the way through the bearing 40. The recess 64 is larger than the collar 59, which allows the bearing 40 to move over a certain range without the collar 59 restricting the movement. As described in detail below, the collar 59, in combination with the recess 64, restricts articulation (lateral bending and anterior/posterior translation) beyond a certain range. In addition, the collar 59 and recess 64 prevent subluxation of the bearing 40.

Figure 7:
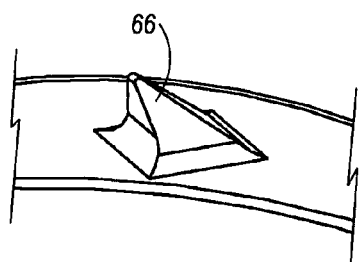
FIG. 7 is an enlarged view of one of the barbed teeth shown in FIG. 6.

FIG. 6 is an assembled isometric view of the artificial disc 30 shown in FIGS. 4 and 5 from an anterior direction. As shown, the bearing 40 simultaneously engages the end plate 36 and the end plate 38. The outer surfaces 42 and 50 of the end plates 36 and 38 also include a plurality of barbed teeth 66, configured to prevent anterior expulsion of the artificial disc 30. FIG. 7 is an enlarged view of one of the barbed teeth 66 shown in FIG. 6.

When designing an artificial disc, it is important to consider proper fit of the disc, and proper fixation to the bone. If fixation to the vertebrae is not adequate, there is risk of expulsion of the artificial disc. If the artificial disc does not fit properly (e.g., is too large or too small), there is also a risk of expulsion, as well as risk of pain or damage to the spine, arteries, or nerves. Ensuring a proper fit of an artificial disc may require a surgeon to select an artificial disc having dimensions that most closely fit the patient. In other words, a patient may be fitted with an artificial disc having the dimensions specified by the surgeon. Also note that the examples shown in the drawings illustrate a cervical disc design. Features such as height, width, and footprint would vary, depending on the spinal region or application.

Figure 8:
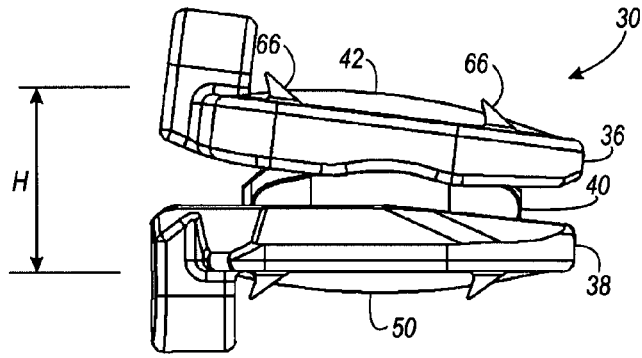
FIGS. 8 and 9 are views illustrating exemplary dimensions of the artificial disc 30.
Figure 9:
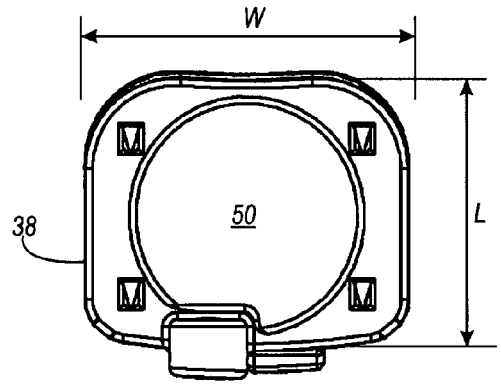

FIGS. 8 and 9 are views illustrating exemplary dimensions of the artificial disc 30. FIG. 8 is a side view of the artificial disc 30, with the left edge of the figure being the anterior side of the disc 30. The height of the artificial disc 30 is designated by the letter "H." As an example, the height of the artificial disc 30 may fall within the range of 6.5-8.0 mm. FIG. 9 is a bottom view of the artificial disc 30, with the lower edge of the figure being the anterior side. The width and length of the artificial disc 30 is designated by the letters "W" and "L." As an example, the length and width of the artificial disc 30 may fall within the ranges of 17-20 mm and 14-17 mm, respectively. Note that these exemplary dimensions are merrily examples, and that the scope of the present invention is not limited to these dimensions. As shown, the length and width of the end plate 38 and 36 control the anatomic footprint, or parameter profile, of the artificial disc 30. Also note that the height of the bearing may also vary, as desired.

Figure 10:
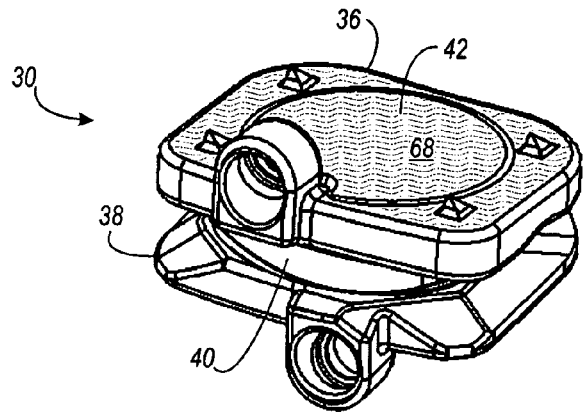
FIG. 10 is and isometric view of the artificial disc, showing in-growth texture.

As mentioned, it is also important that the artificial disc be properly affixed to the vertebrae. As mentioned above, the outer surfaces 42 and 50 of the end plates 36 and 38, respectively, each have convex domed outer surfaces. These domed surfaces on the end plates match the anatomic end plate concavity of the vertebrae to which they are attached. As mentioned above, the barbed teeth 66 dig into the bone, resisting anterior forces, and provide immediate, mechanical post-operative resistance to anterior expulsion. To help the fixation of the end plates 36 and 38 to the bones, the outer surfaces 42 and 50 of the end plates 36 and 38 can be at least partially coated with porous in growth texturing. FIG. 10 is and isometric view of the artificial disc 30. The outer surfaces 42 and 50 of the end plates 36 and 38, respectively, has been treated with porous in-growth texturing to provide longer term bony growth incorporation fixation to the bone. In FIG.

10, the porous in-growth texturing is represented by the shading, and is identified by numeral 68.

Numerous other options are available for supplementing the fixation to the bone. For example, bone screws or pegs can be used to help secure the end plates to the bone. The example mentioned above of a fixation technique using pegs is described in more detail below.

Figure 11A:
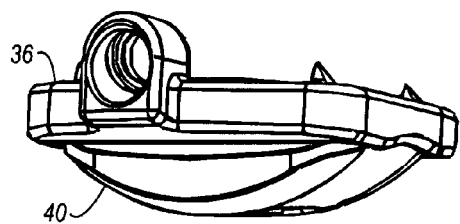
FIGS. 11A, 11B, and 11C are isometric diagrams of the artificial disc of the present invention, illustrating how the bearing is "nested" between the two end plates.
Figure 11B:
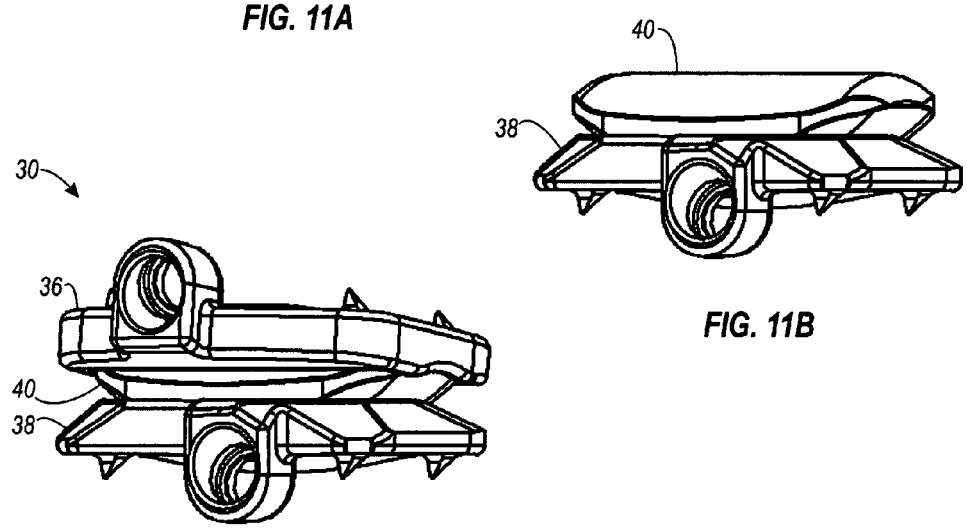
Figure 11C:
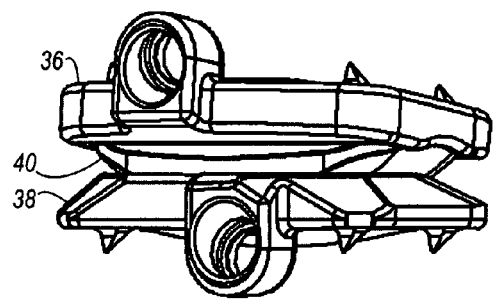
Figure 12:
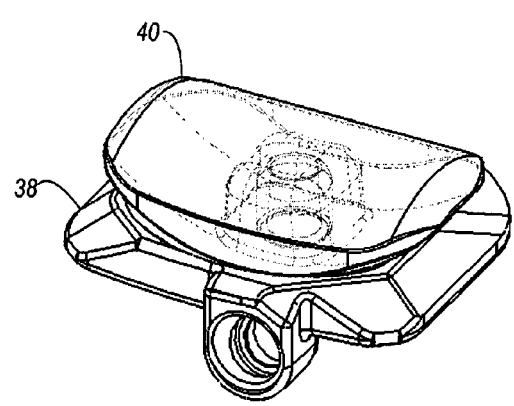
FIG. 12 is a diagram of the lower end plate and the bearing.

The artificial disc of the present invention includes several safety features, in addition to those mentioned above. When the artificial disc is assembled, the bearing is nested in a pocketed upper and lower end plate. This helps to prevent anterior or posterior expulsion of the bearing and/or the artificial disc. FIGS. 11A, 11B, and 11C are diagrams of the artificial disc 30, illustrating how the bearing 40 is "nested" between the end plates 36 and 38. FIG. 11A shows the end plate 36, with the upper surface 48 of the bearing 40 nested in the concave inner surface of the end plate 36. FIG. 11B shows the end plate 38, with the lower surface 60 of the bearing 40 nested in the concave inner surface of the end plate 38. With respect to the interface between the end plate 36 and the bearing 40 (FIG. 11A), the convex surface of the bearing 40 fits within the concave surface of the end plate 36. Likewise, with respect to the interface between the lower end plate 38 and the bearing 40 (FIG. 11B), the convex surface of the bearing 40 fits within the concave surface of the end plate 38. In addition to the bearing being nested or pocketed between the two end plates, the post 58 of the end plate 38 fits within the recess 64 of the bearing 40. FIG. 11C shows the artificial disc 30 of FIGS. 11A and 11B assembled. FIG. 12 is a diagram of the end plate 38 and the bearing 40. For clarity, the end plate 36 is not shown, and the post 58, collar 59, and recess 64 are shown in hidden lines. Since the post 58 and collar 59 are disposed within the recess 64 when the artificial disc is assembled, the post 58 and collar 59 will prevent both anterior and posterior expulsion. Also, the collar 59 and recess 64 restricts movement of the bearing 40 with respect to the end plate 38 (described below).

As mentioned above, flexion/extension articulation in the sagittal plane is unrestricted, while at the same time, curved surfaces of the artificial disc constrain and prevent anterior and posterior subluxation. FIGS. 13-16 are sectional diagrams taken along line 13-13 of FIG. 6, showing the artificial disc 30, with the end plate 36 shown in different positions. FIGS. 13-14 are sectional diagrams illustrating how the artificial disc 30 accomplishes flexion/extension articulation. In this example, the interface between the end plate 38 in the bearing 40 does not contribute to flexion-extension. As shown, the inner concave surface 44 of the end plate 36 matches the convex surface 48 of the bearing 40. In the sagittal plane (plane 14 in FIG. 1), the end plate 36 is allowed to rotate relative to the bearing 40 to provide flexion/extension articulation (arrow 20 in FIG. 1 and in FIG. 13). FIGS. 13 and 14 show the same artificial disc 30, at different points of flexion/extension. The matching curved surfaces of the end plate 36 and bearing 40 allow unrestricted articulation over the possible range of movement.

The configuration of the artificial disc 30 also prevents anterior and posterior subluxation. FIG. 15 is a sectional diagram of the artificial disc 30 illustrating the position of the end plate 36 in an anterior subluxation position. As illustrated, the curves of the end plate 36 and bearing 40 make the subluxation position illustrated in FIG. 15 impossible, as is best illustrated by the intersection of the lines within the circle 70. Similarly, FIG. 16 is a sectional diagram of the artificial disc 30 illustrating the position of the end plate 36 in a posterior subluxation position. As illustrated, the curves of the end plate 36 and bearing 40 make the subluxation position illustrated in FIG. 16 impossible, as is best illustrated by the intersection of the lines within the circle 72.

Figure 17:
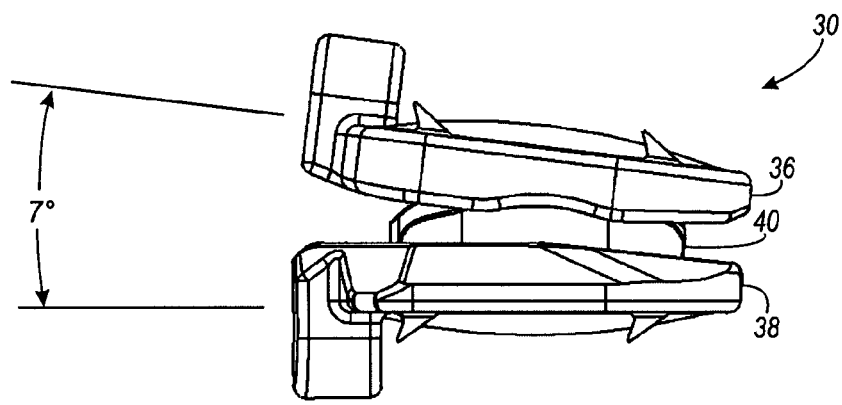
FIGS. 17-19 illustrate an exemplary range of flexion/extension articulation of the artificial disc of the present invention.
Figure 18:
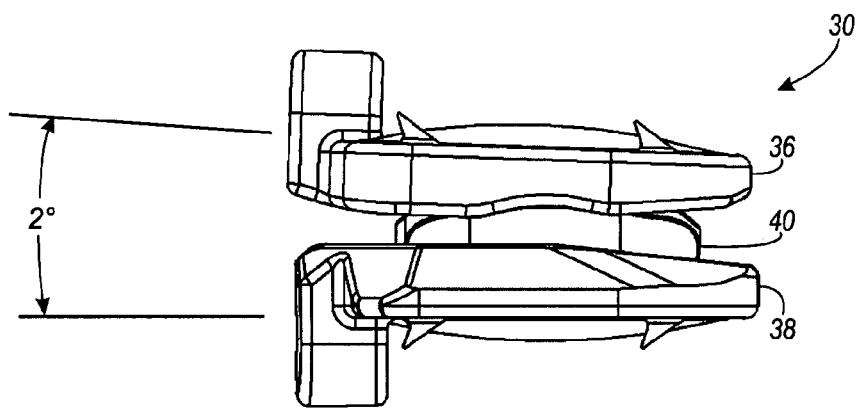
Figure 19:
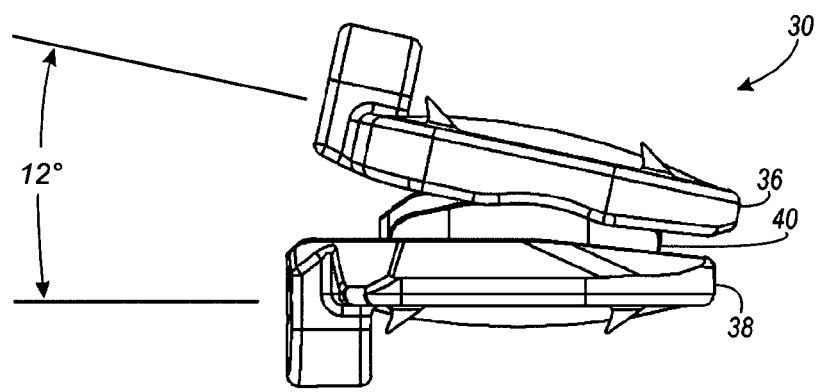

The artificial disc 30 facilitates flexion/extension over a range that is defined by the specific configuration of the artificial disc 30. FIGS. 17-19 illustrate an exemplary range of flexion/extension articulation. Of course, the artificial disc 30 can be configured to allow any desired range of motion. FIG. 17 illustrates a neutral or nominal position, which in this example, the end plate 36 is positioned at a 7° angle relative to the end plate 38. FIG. 18 illustrates a forward position, which in this example, the end plate 36 is positioned at a 2° angle relative to the end plate 38. FIG. 19 illustrates a backward position, which in this example, the end plate 36 is positioned at a 12° angle relative to the end plate 38. In this example, the artificial disc 30 has a flexion/extension range of approximately 10°, or 5° each direction from the nominal position.

Figure 20:
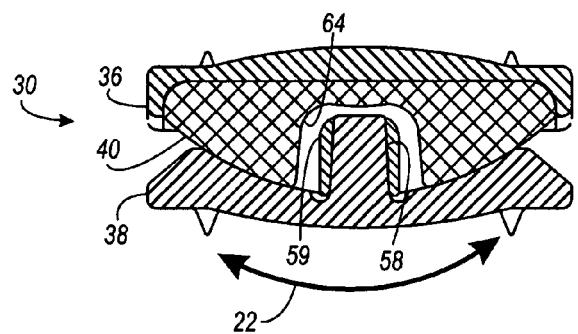
FIGS. 20-24 are sectional diagrams taken along line 20-20 of FIG. 6, with one end plate shown in different positions.
Figure 21:
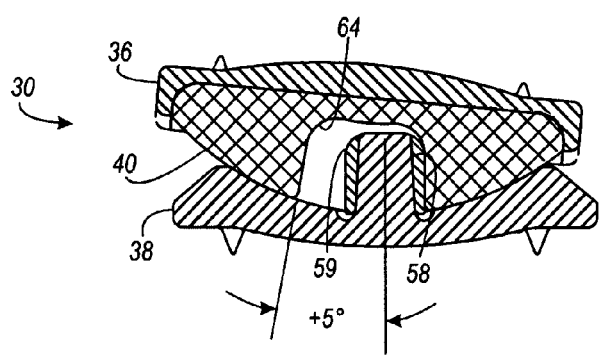
Figure 22:
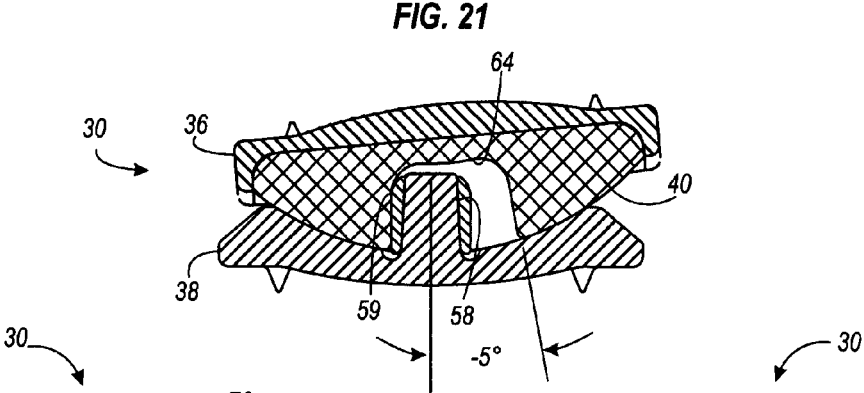

As mentioned above, lateral bending articulation in the coronal plane is unrestricted, while at the same time, curved surfaces of the artificial disc constrain and prevent medial lateral subluxation/translation. FIGS. 20-22 are sectional diagrams illustrating how the artificial disc 30 accomplishes lateral bending articulation. In this example, the interface between the end plate 36 and the bearing 40 does not contribute to lateral bending. While the concave inner surface 52 of the end plate 38 does not match the lower surface 60 of the bearing 40, the middle portion 54 of the concave inner surface 52 and the middle portion 62 of the lower surface 60 have the same radius of curvature. In the coronal plane (plane 12 in FIG. 1), the bearing 40 is allowed to rotate relative to the end plate 38 to provide lateral bending (arrow 22 in FIG. 1 and in FIG. 20). FIGS. 21 and 22 show the same artificial disc 30, at different points of lateral bending.

The curved surfaces making up the middle portions 54 and 62 of the end plate 38 and bearing 40, respectively, allow unrestricted lateral bending articulation over a possible range of movement. Lateral bending is restricted in the artificial disc 30 by the configuration of the collar 59 placed over the post 58 of the end plate 38, and the recess 64 formed in the bearing 40. The artificial disc 30 is configured to allow unrestricted and unconstrained lateral bending articulation, until a wall of the recess 64 engages the collar 59.

The range of lateral bending of the artificial disc 30 is controlled by the configuration of its components. FIGS. 20-22 illustrate an exemplary range of lateral bending articulation. Of course, the artificial disc 30 can be configured to allow any desired range of motion. FIG. 20 illustrates the artificial disc 30 in a neutral or nominal position. FIG. 21 illustrates lateral bending to one extreme, which in this example, is +5° from the position shown in FIG. 20. FIG. 22 illustrates lateral bending to the opposite extreme, which in this example, is −5° from the position shown in FIG. 20. It is evident by looking at FIGS. 20-22, at the lateral bending range can be chosen by configuring the space between the recess 64 and the collar 59. In other words, a larger collar 59, and/or a smaller recess 64, will result in a smaller lateral bending range. Likewise, a smaller collar 59, and/or a larger recess 64 will result in a larger lateral bending range.

Figure 23:
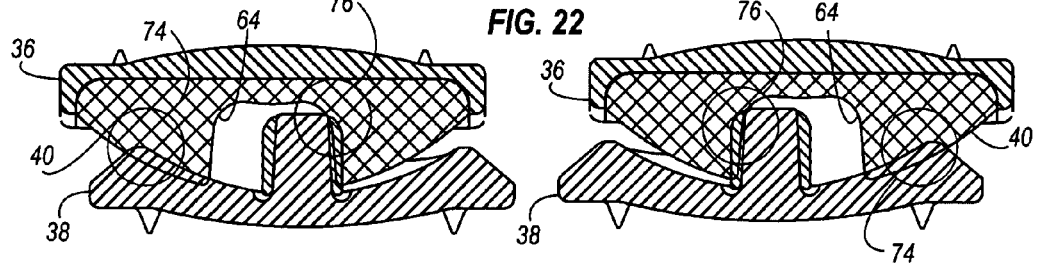
Figure 24:
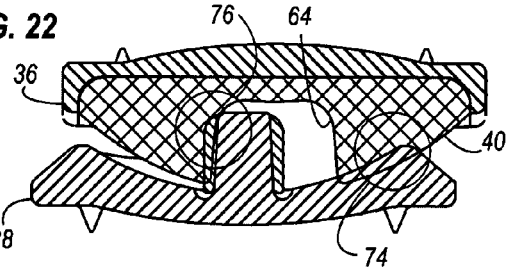

The configuration of the artificial disc 30 also prevents medial lateral subluxation. FIGS. 23 and 24 are sectional diagrams of the artificial disc 30 illustrating the end plate 36 in opposite medial lateral subluxation positions. As illustrated, the curves of the end plate 38 and bearing 40 make the medial lateral subluxation positions, as illustrated in FIGS. 23 and 24, impossible, as is best illustrated by the intersection of the lines within the circles 74. In addition, the post 58, and collar 59 also prevent medial lateral subluxation, as is best illustrated by the intersection of the lines within the circles 74 and 76 in FIGS. 23 and 24.

Figure 25:
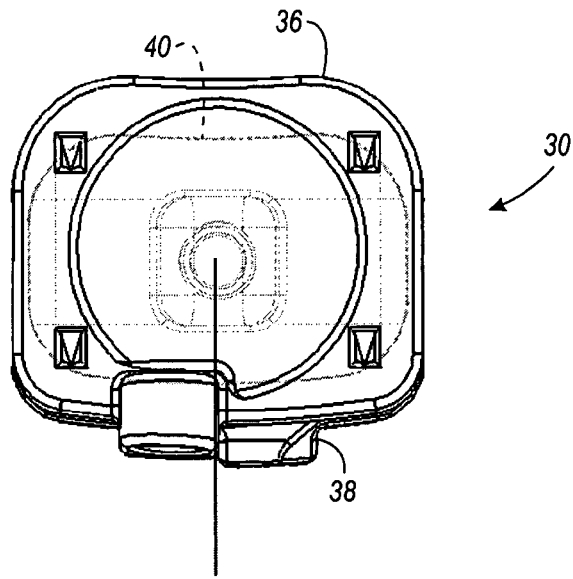
FIGS. 25-27 are top views of an artificial disc of the present invention, illustrating how the artificial disc enables axial rotation.
Figure 26:
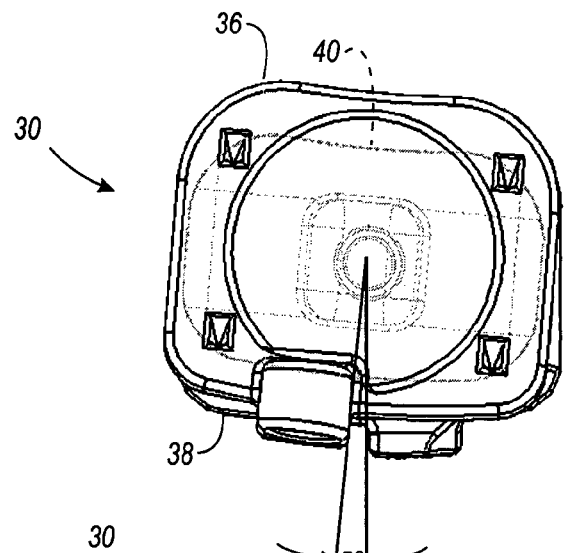
Figure 27:
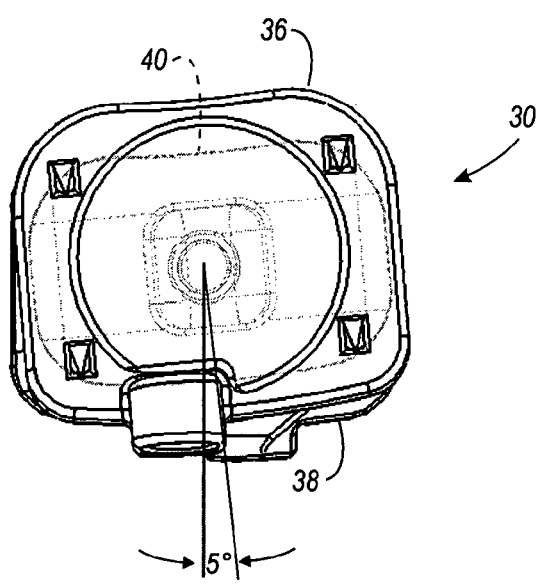

As mentioned above, axial rotation articulation about an axis that is perpendicular to the transverse plane 16 is constrained. FIGS. 25-27 are top views of an artificial disc 30, illustrating how the artificial disc 30 accomplishes axial rotation. In this example, the interface between the end plate 36 and the bearing 40 does not contribute to axial rotation. While the concave inner surface 52 of the end plate 38 does not match the lower surface 60 of the bearing 40, the interface between the bearing 40 and end plate 38 allows some degree of rotation. As the bearing 40 rotates relative to the end plate 38, the axial rotation will be constrained by the curved surfaces of the lower surface 60 of the bearing 40 engaging the curved outer portions 56 of the end plate 38 (FIGS. 4 and 5).

The range of axial rotation is controlled by the configuration of the lower surface 60 of the bearing 40 and the concave inner surface 52 of the end plate 38. In one example, the allowable axial rotation is +/−5°. FIG. 25 shows the artificial disc 30 in a normal, unrotated position. FIG. 26 shows the artificial disc 30 rotated in one direction by 5°. FIG. 27 shows the artificial disc 30 rotated in the opposite direction by 5°.

FIGS. 28-32 are sectional diagrams taken along line 13-13 of FIG. 6 that illustrate anterior and posterior translation of an artificial disc of the present invention. Referring back to FIGS. 4 and 5, the middle portion 62 of the bearing 40 is narrower than the middle portion 54 of the end plate 38. As mentioned above, the middle portions 54 and 62 are each flat in one direction and share the same curvature radius in the other direction.

Figure 28:
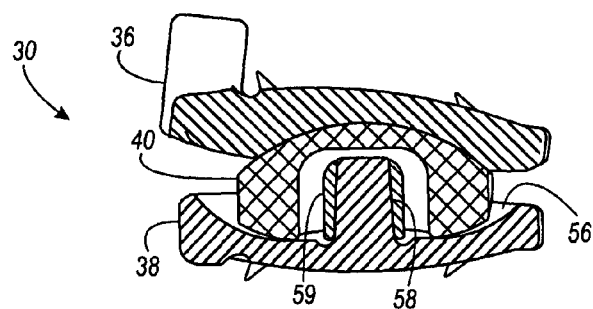
FIGS. 28-32 are sectional diagrams taken along line 13-13 of FIG. 6 that illustrate anterior and posterior translation of an artificial disc of the present invention.
Figure 29:
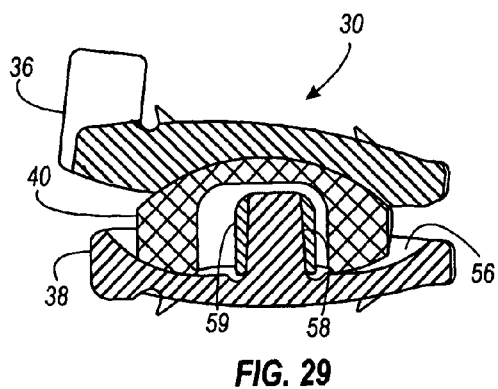
Figure 30:
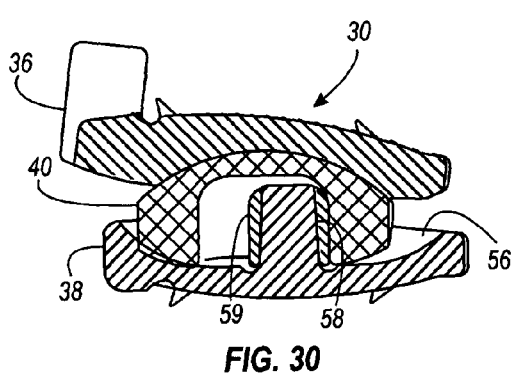

FIG. 28 is a sectional diagram of the artificial disc 30 in a neutral position. As shown, the middle portion 62 of the bearing 40 rests on the middle portion 54 of the end plate 38. Since the middle portion 62 is narrower than the middle portion 54, the bearing 40 can slide relative to the end plate 38, in an anterior and posterior direction. Over a relatively small range, translation articulation is unconstrained. However, the outer portions 56 of the end plate 38 will eventually engage the lower surface 60 of the bearing 40 to constrain the translation articulation. Furthermore, the post 58 and collar 59 restrict anterior and posterior translation when the collar 59 engages one of the walls of the recess 64. FIG. 29 illustrates anterior translation, which is unrestricted up to the point shown in FIG. 29. As mentioned above, the curvature of the outer portions 56 of the end plate 38 will restrict the bearing 40 once the bearing 40 has moved to a certain distance. FIG. 30 illustrates further anterior translation, up to the point where the wall of the recess 64 engages the collar 59.

Figure 31:
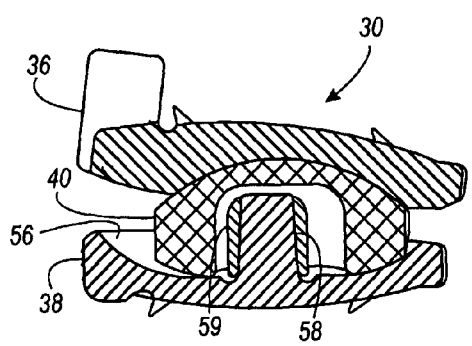
Figure 32:
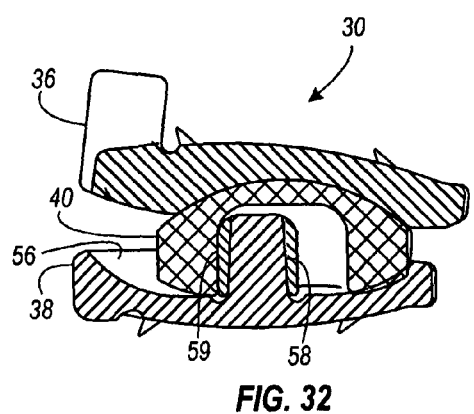

FIG. 31 illustrates posterior translation, which is also unrestricted up to the point shown in FIG. 31. FIG. 32 illustrates further posterior translation, up to the point where the wall of the recess 64 engages the collar 59. The various dimensions and configurations of the artificial disc 30 control the range of anterior and posterior translation, and can be configured to any desired range. In one example, the unrestricted translation range is 0.5 mm in either direction. In this example, the artificial disc 30 is configured such that the collar 59 will engage the recess 64 1 mm in either direction from the neutral position. Of course, various other ranges are also possible.

Figure 33:
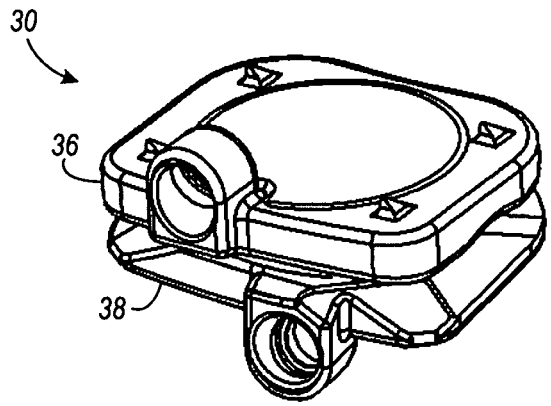
FIGS. 33-35 are isometric views of an artificial disc of the present invention, illustrating three examples of simultaneous and independent degrees of freedom.
Figure 34:
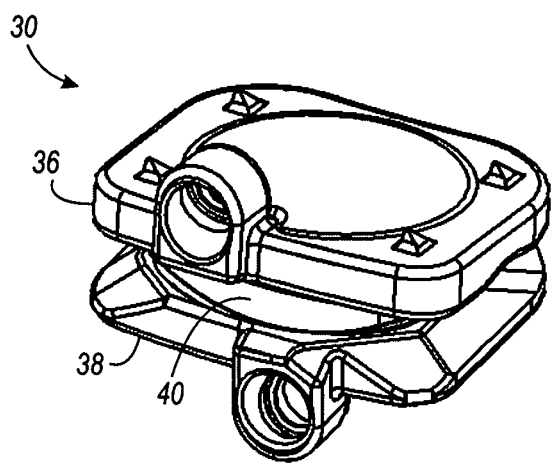
Figure 35:
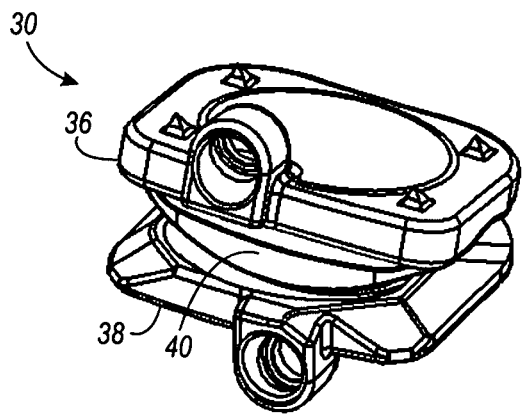

As described above in shown in figures, an artificial disc of the present invention is capable of simultaneous and independent articulation of flexion/extension, lateral bending, anterior/posterior translation, and axial rotation. In addition, various articulations of the artificial disc of the present invention are constrained and restricted, where desired. Each degree of freedom of the artificial disc is independently designed to match the needs desired by a user. FIGS. 33-35 are isometric views of an artificial disc of the present invention, illustrating three examples of simultaneous and independent degrees of freedom. FIG. 33 shows an example with the flexion/extension articulation position at 2° (see FIG. 18), the axial rotation is at +5° (see FIG. 26), the anterior/posterior translation is at +1 mm (see FIG. 30), and the lateral bending is at +5° (see FIG. 21). FIG. 34 shows an example with the flexion/extension articulation position at 7° (see FIG. 17), the axial rotation is at 0° (see FIG. 25), the anterior/posterior translation is at 0 mm (see FIG. 28), and the lateral bending is at 0° (see FIG. 20). FIG. 35 shows an example with the flexion/extension articulation position at 12° (see FIG. 19), the axial rotation is at −5° (see FIG. 27), the anterior/posterior translation is at −1 mm (see FIG. 32), and the lateral bending is at −5° (see FIG. 22). It is evident that each type of articulation can be simultaneously and independently achieved with an artificial disc of the present invention.

Figure 36:
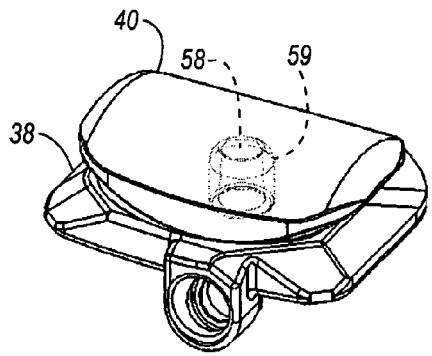
FIG. 36 is an isometric diagram of the end plate and bearing, with the post and collar shown in dashed lines.

As described above, the present invention includes the post 58 and collar 59 extending from the end plate 38 into the recess 64 of the bearing 40 to prevent subluxation of the bearing 40, and to restrict the movement of the bearing 40. Following is a more detailed description of the collar 59, including variations of the collar. FIG. 36 is an isometric diagram of an end plate 38 and a bearing 40. For clarity, the opposing end plate 36 is not shown. The post 58 and collar 59 are shown using hidden lines. The space disposed between the walls of the recess 64 and the collar 59 determines the amount of movement the bearing 40 can make relative to the end plate 38, before a wall of the recess 64 engages the collar 59.

Figure 37:
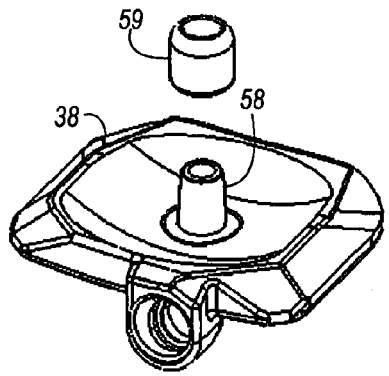
FIG. 37 is an exploded view of an end plate and a collar of the present invention.

One aspect of the present invention relates to customizing the configuration of the artificial disc to suit the needs of a patient. FIG. 37 is an exploded view of the end plate 38 and the collar 59. As shown, the collar 59 is configured to be placed over the post 58. In addition, the collar 59 can interface with the end plate 38 via a locking taper (see FIGS. 38 and 39). Since, in this example, the collar 59 is removable, the artificial disc can be used with various types and sizes of collars 59 to achieve the desired amount and type of articulation.

Figure 38:
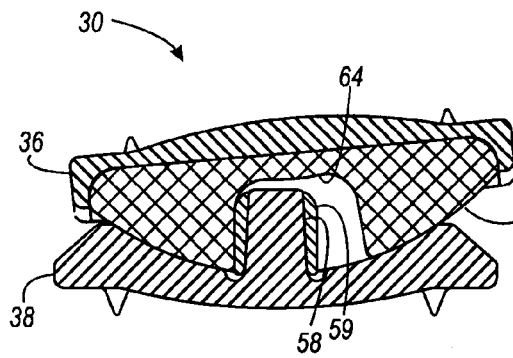
FIGS. 38 and 39 are sectional diagrams illustrating two examples of collars.
Figure 39:
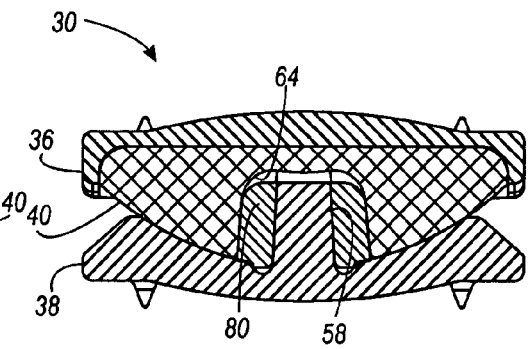

In one example, the size (e.g., diameter) of the collar 59 can be varied to achieve a desired result. For example, FIG. 38 is a sectional diagram of an artificial disc 30, similar to the view shown in FIG. 22. FIG. 39 is a sectional diagram of the artificial disc 30, with a different collar installed. As shown, the collar 80 shown in FIG. 39 is larger than the collar 59 shown in FIG. 38. As a result, the artificial disc 30 shown in FIG. 39 has different articulating characteristics. With a larger collar, such as collar 80, the artificial disc 30 is more restricted, and will have a shorter articulation range for lateral bending and anterior and posterior translation. Note that the flexion/extension articulation is not affected. A larger collar, such as collar 80, may be desired for patients who are less stable and who would benefit from a more restrictive disc.

Figure 40B:
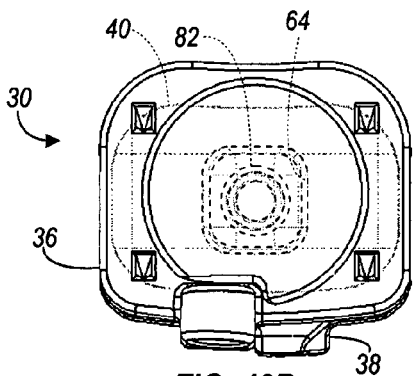
FIGS. 40A, 40B, 41A and 41B show additional examples of collars for an artificial disc of the present invention.
Figure 40A:
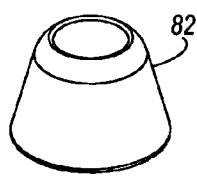
Figure 41B:
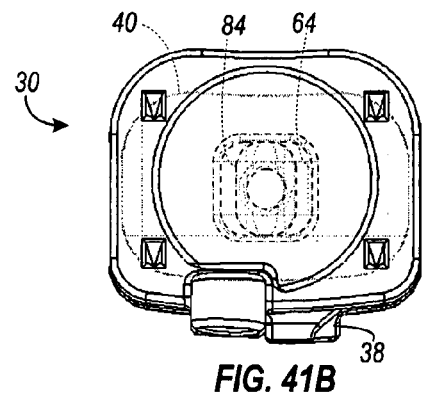
Figure 41A:
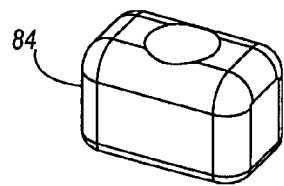

FIGS. 40A and 40B illustrate another collar configuration. FIG. 40A is an isometric diagram showing a collar 82 that has a tapered diameter to provide various changes in articulations. FIG. 40B is a top view of the artificial disc 30, showing the collar 82, and the recess 64 in dashed lines. FIG. 41A is an isometric diagram showing another collar configuration. In this example, the collar 84 is rectangular in shape. The rectangular collar 84 can be configured to either restrict translation and allow lateral bending, or to allow translation and restrict lateral bending. FIG. 41B is a top view of the artificial disc 30, showing the collar 84, and the recess 64 in dashed lines. As shown, the space between the collar 84 and recess 64 is different on different sides, since the collar 84 is not symmetrical. In the example shown in FIG. 41B, translation is more restricted than the examples described above. If the collar 84 were rotated 90°, lateral bending would be more restricted. Various other types of collars are also possible for use with the present invention.

Figure 42:
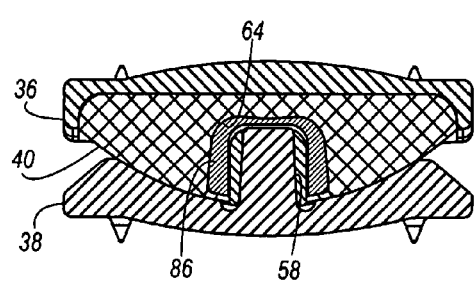
FIGS. 42 and 43 are diagrams illustrating an interior collar of the present invention.
Figure 43:
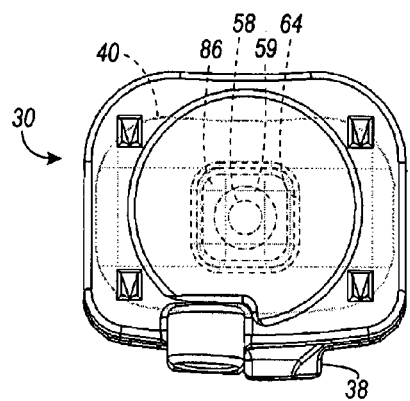

FIG. 42 is a diagram of another type of collar that accomplishes the same thing as the collars described above. In this example, rather than providing a collar that fits around the post 58, an internal collar 86 is provided that fits within the walls of the recess 64 of the bearing 40. When the bearing 40 moves relative to the end plate 38, the movement will be restricted once the internal collar 86 comes into contact with the collar 59. If the collar 59 is not used, then the movement will be restricted once the internal collar 86 comes into contact with the post 58. FIG. 43 is a top view of the artificial disc 30, showing the internal collar 86, collar 59, and post 58 using hidden lines.

As mentioned above while describing FIG. 3, the artificial disc of the present invention may be affixed to the vertebrae of the spine using pegs. After drilling holes into the vertebrae (with the artificial disc already positioned), the pegs 32 are inserted through the openings 37 and 39 of the end plates and 36 and 38 and into the holes drilled into the vertebrae. Once the pegs 32 are in place, locking screws 34 are threaded into threaded recesses formed in the pegs, to lock the pegs in place (described in more detail below). One advantage of using the pegs 32 rather than typical bone screws, is that bone screws will tend to cause the artificial disc to migrate as the screws are tightened. By using pegs 32, this migration is eliminated. The angle of the pegs 32 also help to prevent migration, since the pegs are at different angles from one another, and are not parallel to artificial disc.

Figure 44:
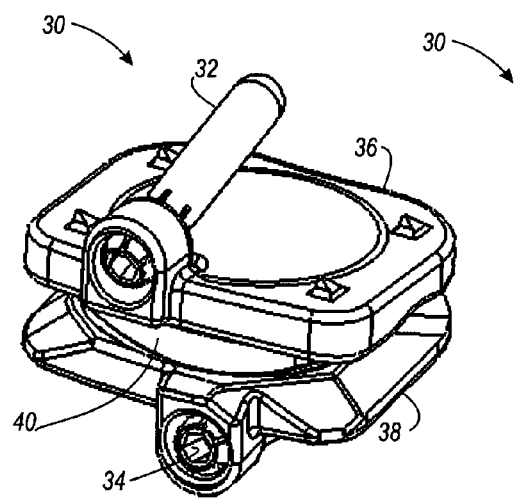
FIGS. 44-46 are views of an artificial disc of the present invention with fixation pegs installed.
Figure 45:
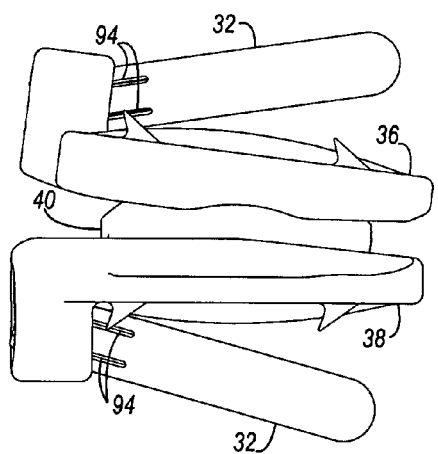
Figure 46:
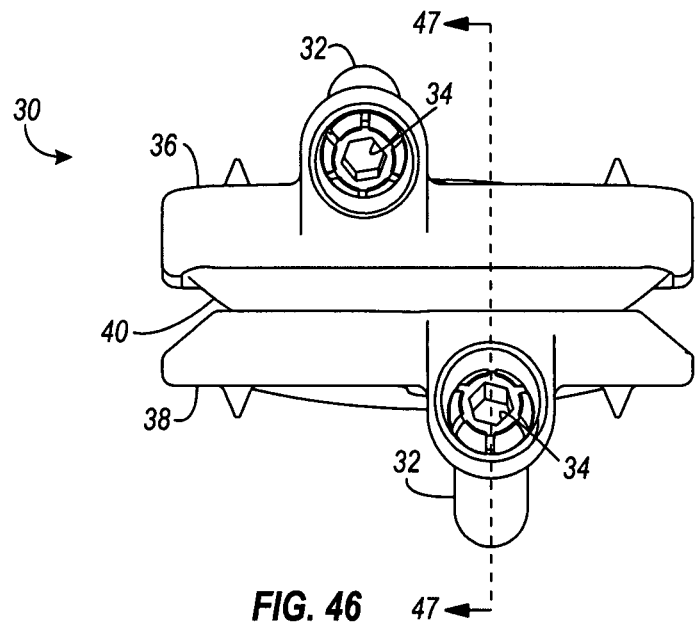
Figure 47:
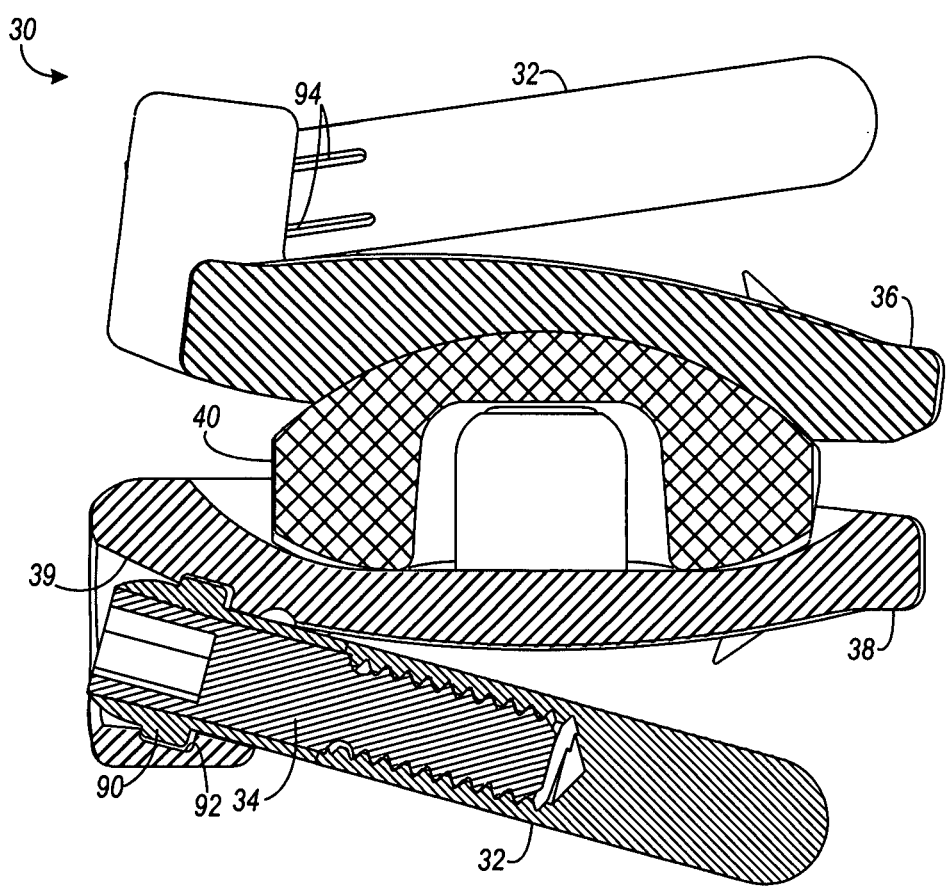
FIG. 47 is a sectional view of an artificial disc of the present invention, showing details of the peg and locking screw.

FIG. 44 is an isometric view of an artificial disc 30, including the pegs 32, and locking screws 34 in an installed position. FIG. 45 is a side view of the artificial disc shown in FIG. 44. FIG. 46 is a front anterior view of the artificial disc shown in FIG. 44. FIG. 47 is a sectional view of the artificial disc shown in FIG. 44, taken along lines 47-47 of FIG. 46. As shown in FIG. 47, the peg 32 includes annular protrusions 90 disposed near the end of the peg 32. The hole 39 of the end plate 38 has an annular groove 92 formed in it that is adapted to receive the annular protrusions 90 of the peg 32. Due to the plurality of slots 94 formed in the peg 32, the head of the peg is expandable, and the annular protrusions 90 can snap into the annular groove 92 when the peg 32 is inserted into the hole 39 of the end plate 38. The locking screws 34 are tapered slightly, which causes the peg head to expand when the locking screws 34 are screwed into the pegs 32. When the peg head expands due to the tapered locking screws 34, the annular protrusions 90 will be pressed into the annular groove 92, locking the peg 32 in place. The other peg shown in FIG. 47 is installed into the hole 37 of the end plate 36 in the same manner.

Figure 48:
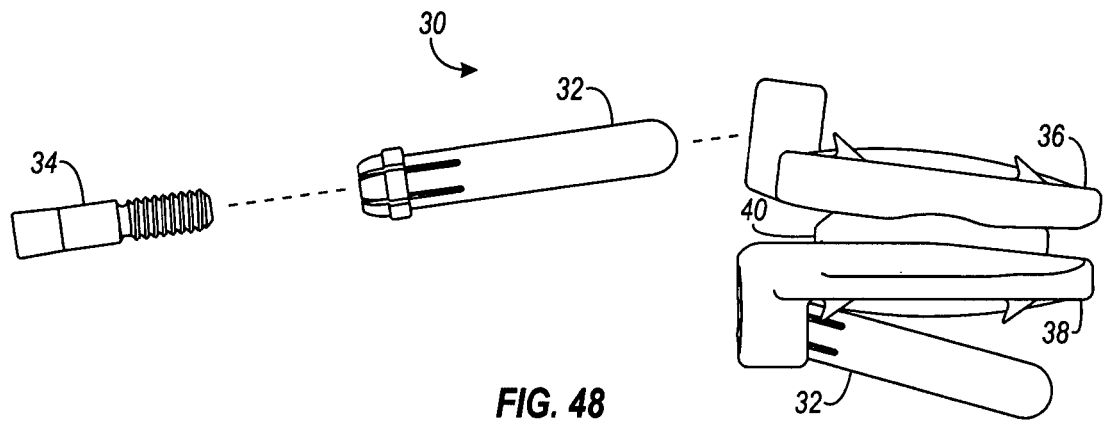
FIGS. 48 and 49 are exploded view illustrating how the pegs are installed.
Figure 49:
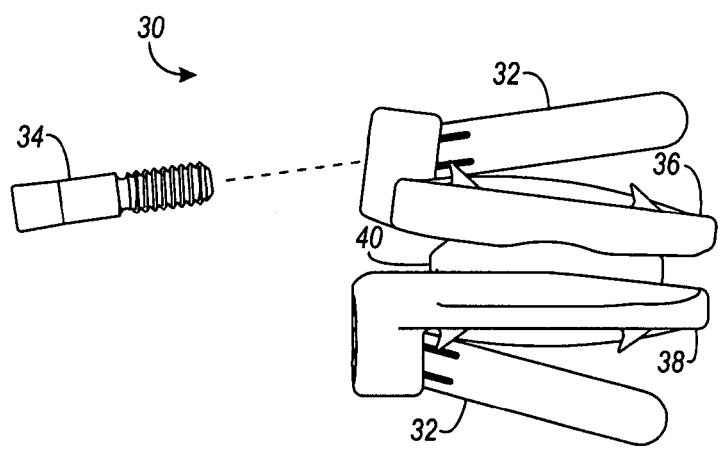

FIGS. 48 and 49 are exploded views illustrating the installation of the pegs 32 to the artificial disc 30. FIG. 48 shows a first peg 32 already installed into end plate 38. As mentioned above, once the artificial disc 30 is inserted between two adjacent vertebrae (FIGS. 2 and 3), the surgeon drills holes into the vertebrae. Next, a peg 32 is inserted into the hole 37 of the end plate 36, and into the hold drilled in the bone (FIG. 49). Next, a locking screw 34 is screwed into a threaded hole in the peg 32 (see FIG. 47), locking the peg in place.

Figure 50:
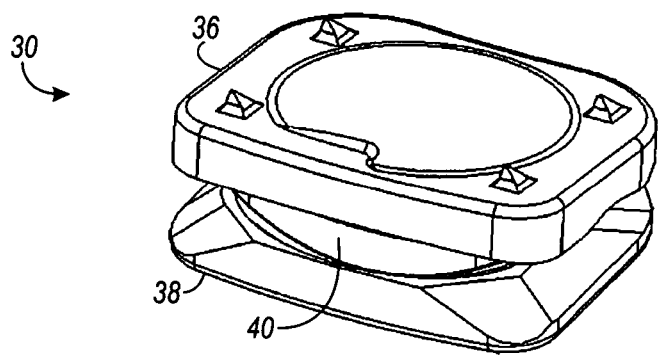
FIG. 50 is an isometric view of another example of an artificial disc of the present invention

As mentioned above, various ways are possible of affixing an artificial disc of the present invention to the vertebrae. In one example, bone screws are used in place of pegs. In another example, an artificial disc uses bone fixation, and the teeth 66. FIG. 50 is an isometric diagram of an artificial disc that is similar to the discs described above, but configured to use without pegs or bone screws. Also note that the peg and locking screw assembly described above is not limited to artificial disc. The pegs of the present invention may be used with any desired type of surgical implant.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

What is claimed is:

1. A surgical implant configured to be inserted between two vertebrae comprising:
    a first member configured to be attachable to a first vertebrae, said first member having a cylindrically-shaped concave surface with no protrusions;
    a second member configured to be attachable to a second vertebrae, said second member having a cylindrically-shaped concave surface, and further comprising a protrusion;
    a third member disposed between the first and second members to form an articulating artificial disc, the third member having an upper cylindrically-shaped convex surface adapted to engage to the cylindrically-shaped concave surface of the first member and a lower cylindrically-shaped convex surface adapted to engage to the cylindrically-shaped concave surface of the second member, wherein the upper and lower cylindrically-shaped convex surfaces of the third member are immovable with respect to one another, and wherein the lower cylindrically-shaped convex surface comprises a recess and the upper cylindrically-shaped convex surface does not comprise a recess;
    a first peg comprising:
        an internally threaded cavity formed into a proximal end of the first peg; and
        a non-threaded external surface that extends along an entire length of the first peg;
    a second peg comprising:
        an internally threaded cavity formed into a proximal end of the second peg; and
        a non-threaded external surface that extends along an entire length of the second peg;
    a first locking screw adapted to threadably engage the internally threaded cavity of the first peg;
    a second locking screw adapted to threadably engage the internally threaded cavity of the second peg;
    wherein the first member is securable to the first vertebra via the first peg and the second member is securable to the second vertebra via the second peg; and
    wherein the protrusion extends from the second member to the recess in the lower cylindrically-shaped convex surface of the third member and further wherein a collar is fitted over the protrusion.

2. The surgical implant of claim 1, wherein the first member and the third member are configured to allow flexion/extension of the artificial disc, and wherein the second member and the third member are configured to allow lateral bending, translation, and rotation of the surgical implant.

3. The surgical implant of claim 2, wherein each articulation of the surgical implant is constrained.

4. The surgical implant of claim 1, wherein the first and second members are securable to the first and second vertebrae by bony adherence to the first and second vertebrae.

5. The surgical implant of claim 1, wherein the first and second members are configured to attach to the first and second vertebrae through sides of the first and second vertebrae using the first and second pegs and first and second locking screws.

6. A surgical implant configured to be inserted between two vertebrae comprising:
a first member configured to be attachable to a first vertebrae, the first member having a first cylindrically-shaped concave surface with no protrusions;
a second member configured to be attachable to a second vertebrae, the second member having a second cylindrically-shaped concave surface, and further comprising a protrusion;
a third member disposed between the first and second members, the third member having first and second cylindrically-shaped convex surfaces configured to engage the first and second cylindrically-shaped concave surfaces, respectively, wherein the first and second cylindrically-shaped convex surfaces are immovable with respect to one another and wherein the second cylindrically-shaped convex surface comprises a recess and the first cylindrically-shaped convex surface does not comprise a recess;
a first peg comprising:
an internally threaded cavity formed into a proximal end of the first peg; and
a non-threaded external surface that extends along an entire length of the first peg;
a second peg comprising:
an internally threaded cavity formed into a proximal end of the second peg; and
a non-threaded external surface that extends along an entire length of the second peg;
a first locking screw adapted to threadably engage the internally threaded cavity of the first peg;
a second locking screw adapted to threadably engage the internally threaded cavity of the second peg;
wherein the first member is securable to the first vertebra via the first peg and the second member is securable to the second vertebra via the second peg;
wherein the protrusion extends from the second member to the recess in the second cylindrically-shaped convex surface of the third member and further wherein a collar is fitted over the protrusion; and
wherein the first cylindrically-shaped convex surface of the third member and the first cylindrically-shaped concave surface of the first member are configured to facilitate flexion/extension of the surgical implant; and wherein the second cylindrically-shaped convex surface of the third member and the second cylindrically-shaped concave surface of the second member are configured to facilitate lateral bending, translation, and rotation of the third member.

7. The surgical implant of claim 6, wherein the protrusion and the recess are sized to allow lateral bending over a range before being restricted by the protrusion engaging a side wall defined by the recess.

8. The surgical implant of claim 7, wherein the lateral bending is constrained over the range.

9. The surgical implant of claim 6, wherein the protrusion and the recess are sized to allow translation over a range before being restricted by the collar engaging a side wall defined by the recess.

10. The surgical implant of claim 6, further comprising a protrusion extending from the third member to restrict the of the third member relative to the second member.

11. The surgical implant of claim 6, wherein the second cylindrically-shaped concave surface and the second cylindrically-shaped convex surface include matching straight portions to facilitate translation.

12. The surgical implant of claim 11, wherein the straight portion of the second cylindrically-shaped concave surface is wider than the straight portion of the second cylindrically-shaped convex surface.

13. The surgical implant of claim 12, wherein the second cylindrically-shaped concave surface includes first and second angled surfaces extending upward from opposite sides of the straight portion of the second cylindrically-shaped concave surface to constrain translation articulation.

14. The surgical implant of claim 6, wherein the second cylindrically-shaped concave surface is configured to constrain rotation of the third member relative to the second member.

15. The surgical implant of claim 6, wherein the first cylindrically-shaped concave surface and the first cylindrically-shaped convex surface are configured to allow flexion and to restrict lateral bending and rotation, relative to the first and second members.

16. The surgical implant of claim 15, wherein the first cylindrically-shaped concave surface and the first cylindrically-shaped convex surface are configured to allow unconstrained flexion over a range of motion.

17. The surgical implant of claim 6, wherein the first and second members are securable to the first and second vertebrae by bony adherence to the first and second vertebrae.

18. The implant of claim 6, wherein the first and second members are configured to attach to the first and second vertebrae through sides of the first and second vertebrae using the first and second pegs and first and second locking screws.

19. A method of providing an artificial disc to treat a damaged disc in a spine comprising:
providing a first member configured to be attachable to a first vertebrae, said first member having a cylindrically-shaped concave surface with no protrusions;
providing a second member configured to be attachable to a second vertebrae, said second member having a cylindrically-shaped concave surface, and further comprising a protrusion;
providing a third member between the first and second members, the third member having an upper cylindrically-shaped surface adapted to engage the first member and a lower cylindrically-shaped surface adapted to engage the second member, wherein the upper and lower cylindrically-shaped surfaces of the third member are immovable with respect to one another, wherein the lower cylindrically-shaped surface comprises a recess and the upper cylindrically-shaped surface does not comprise a recess, and wherein the protrusion extends from the second member to the recess in the lower cylindrically-shaped surface of the third member and further wherein a collar is fitted over the protrusion; and
configuring the first and second members and the third member to allow the artificial disc simultaneous and independent articulation of flexion/extension, lateral bending, anterior/posterior translation, and axial rotation; and
securing the first and second members to the first and second vertebrae by inserting a first peg through the first member and into the first vertebrae and screwing a first locking screw into a bore of the first peg to lock the first peg in place, wherein the first peg comprises an external non-threaded surface that extends along an entire length of the first peg, and inserting a second peg through the second member and into the second vertebrae and screwing a second locking screw into a bore of the second peg to lock the second peg in place, wherein the first peg comprises an external non-threaded surface that extends along an entire length of the first peg.

20. The method of claim 19, further comprising configuring the protrusion and the recess to allow lateral bending over a range before being restricted by the protrusion when the collar engages a wall defined by the recess.

21. The method of claim 20, wherein the lateral bending is constrained over the range.

22. The method of claim 19, further comprising configuring the protrusion and the recess to allow translation over a range before being restricted by the protrusion when the collar engages a wall defined by the recess.

23. The method of claim 19, further comprising configuring the first member and the third member to allow flexion/extension of the artificial disc, and configuring the second member and the third member to allow lateral bending, translation, and rotation of the artificial disc.

24. The method of claim 23, further comprising constraining each articulation of the artificial disc.

25. The method of claim 19, further comprising securing the first and second members to the first and second vertebrae by bony adherence to the first and second vertebrae.

26. The method of claim 19, wherein the first and second members are configured to attach to the first and second vertebrae through sides of the first and second vertebrae using the first and second pegs and first and second locking screws.

27. A surgical implant configured to be inserted between two vertebrae comprising:
 a first member configured to be attachable to a first vertebrae, said first member having a cylindrically-shaped concave surface with no protrusions;
 a second member configured to be attachable to a second vertebrae, said second member having a cylindrically-shaped concave surface, and further comprising a protrusion;
 a third member disposed between the first and second members;
 a first peg comprising:
  an internally threaded cavity formed into a proximal end of the first peg; and
  a non-threaded external surface that extends along an entire length of the first peg;
 a second peg comprising:
  an internally threaded cavity formed into a proximal end of the second peg; and
  a non-threaded external surface that extends along an entire length of the second peg;
 a first locking screw adapted to threadably engage the internally threaded cavity of the first peg;
 a second locking screw adapted to threadably engage the internally threaded cavity of the second peg;
  wherein the first member is securable to the first vertebra via the first peg and the second member is securable to the second vertebra via the second peg;
 wherein the third member has a first cylindrically-shaped surface configured to engage the first member to facilitate movement of the surgical implant about a first axis that is substantially horizontal;
 wherein the third member has a second cylindrically-shaped surface configured to engage the second member to facilitate movement about a second axis that is substantially vertical, wherein the first and second axes are substantially perpendicular to one another, and wherein the first and second cylindrically-shaped surfaces of the third member are immovable with respect to one another, wherein the second cylindrically-shaped surface comprises a recess and the first cylindrically-shaped surface does not comprise a recess, and wherein the protrusion extends from the second member to the recess in the second cylindrically-shaped surface of the third member and further wherein a collar is fitted over the protrusion; and
 wherein the first and second members are movable relative to one another to facilitate anterior/posterior translation, and axial rotation.

28. The surgical implant of claim 27, wherein movement about the first axis is flexion/extension.

29. The surgical implant of claim 28, wherein movement about the second axis is lateral bending.

30. The surgical implant of claim 27, wherein the first and second axes are movable relative to the second member to facilitate translation.

31. The surgical implant of claim 27, wherein the first and second axes are rotatable relative to the second member to facilitate axial rotation.

32. The surgical implant of claim 27, further comprising:
 wherein the first cylindrically-shaped surface and the first member are configured to inhibit movement of the surgical implant about the second axis; and
 wherein the second cylindrically-shaped surface and the first member are configured to inhibit movement of the surgical implant about the first axis.

33. The implant of claim 27, wherein the first and second members are configured to attach to the first and second vertebrae through sides of the first and second vertebrae using the first and second pegs and first and second locking screws.

* * * * *